United States Patent
Light et al.

(10) Patent No.: US 6,632,791 B1
(45) Date of Patent: Oct. 14, 2003

(54) THROMBOMODULIN ANALOGS FOR PHARMACEUTICAL USE

(75) Inventors: David Light, San Mateo, CA (US); Michael John Morser, San Francisco, CA (US); Mariko Nagashima, Belmont, CA (US)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/880,484

(22) Filed: Jun. 12, 2001

Related U.S. Application Data

(60) Provisional application No. 60/213,678, filed on Jun. 21, 2000.

(51) Int. Cl.[7] .................. A61K 38/00; C01K 14/00
(52) U.S. Cl. ............................... 514/8; 530/350
(58) Field of Search .............. 514/2, 12, 8; 530/402, 530/412, 417, 380; 435/69.1, 69.6

(56) References Cited

U.S. PATENT DOCUMENTS

| | | |
|---|---|---|
| 5,256,770 A | 10/1993 | Glaser et al. |
| 5,466,668 A | 11/1995 | Glaser et al. |
| 5,863,760 A | 1/1999 | Light et al. |

OTHER PUBLICATIONS

Zhao, L. et al., Identification and Characterization of Two Thrombin–activable Fibrinolysis Inhibitor Isoforms, *Throm. Haemost*, (1998) 80:949–955.

Nagashima, M. et al. "An Inhibitor of Activated Thrombin–Activatable Fibrinolysis Inhibitor Potentiates Tissue–Type Plasminogen Activator–Induced Thrombolysis in a Rabbit Jugular Vein Thrombolysis Model", *Thromb. Res.*, (2000) 98:333–342.

Jackman, R. et al., "Characterization of a thrombomodulin cDNA reveals structural similarity to the low density lipoprotein receptor", *Proc. Natl. Acad. Sci., USA*, (1986) 83:8834–8838.

Jackman R. et al., "Human thrombomodulin gene is intron depleted: Nucleic acid sequences of the cDNA and gene predict protein structure and suggest sites of regulatory control", *Proc. Natl. Acad. Sci, USA* (84):6425–6429.

Nagashima, M. et al., Alanine–scanning Mutagenesis of the Epidermal Growth Factor–like Domains of Human Thrombomodulin Identifies Critical Residues for Its Cofactor Activity, *J. Biol. Chem.*, (1993) 268(4):2888–2892.

Clarke, J., et al., The Short Loop between Epidermal Growth Factor–like Domains 4 and 5 is Critical for Human Thrombomodulin Function, *J. Biol. Chem.*, (1993) 268(9):6309–6315.

Suzuki, K. et al., Structure and expression of human thrombomodulin, a thrombin receptor on endothelium acting as a cofactor for protein C activation, *EMBO J.* (1987) 6(7):1891–1897.

Wang, W. et al. "Comparison of the structures of thrombomodulin requried for the activation of protein C and TAFI", *Fibrinolysis & Proteolysis*, (1998) 12 (1):11, #26.

Adler, M. et al. "The Structure of a 19–Residue Fragment for the C–loop of the Fourth Epidermal Growth Factor–like Domain of Thrombomodulin", *J. of Biol Chem.*, (1995) 270(40):23366–23372.

Kokame, K. et al., "Activation of Thrombin–activable Fibrinolysis Inhibitor Requires Epidermal Growth Factor–like Domain 3 of Thrombomodulin and Is Inhibited Competitively by Protein C", *J. Biol. Chem.*, (1998) 273(20):12135–12139.

Wang, W. et al., Elements of the Primary Structure of Thrombomodulin Required for Efficient Thrombin–activable Fibrinolysis inhibitor Activation, *J. Biol. Chem.* (2000) 275(30):22942–22947.

Hall, S. et al., "Thrombin Interacts with Thrombomodulin, Protein C, and Thrombin–activatable Fibrinolysis Inhibitor via Specific and Distinct Domains", *J. Biol Chem.*, (1999) 274(36):25510–25516.

Glaser, C. et al., "Oxidation of a Specific Methionine in Thrombomodulin by Activated Neutrophil Products Blocks Cofactor Activity", *J. Clin. Invest.* (1992) 90:2565–2573.

Primary Examiner—Karen Cochrane Carlson
Assistant Examiner—Sheridan Snedden
(74) *Attorney, Agent, or Firm*—Wendy L. Washtien

(57) ABSTRACT

The present invention relates to the design, production and use of analogs of thrombomodulin (TM) that have the ability to enhance the thrombin-mediated activation of protein C but which have a significantly reduced ability to promote activation of thrombin-activatable fibrinolysis inhibitor (TAFI). These analogs are useful in, for example, antithrombotic therapy.

16 Claims, 6 Drawing Sheets

Effect of Thrombomodulin (TM) on Coagulation and Fibrinolysis

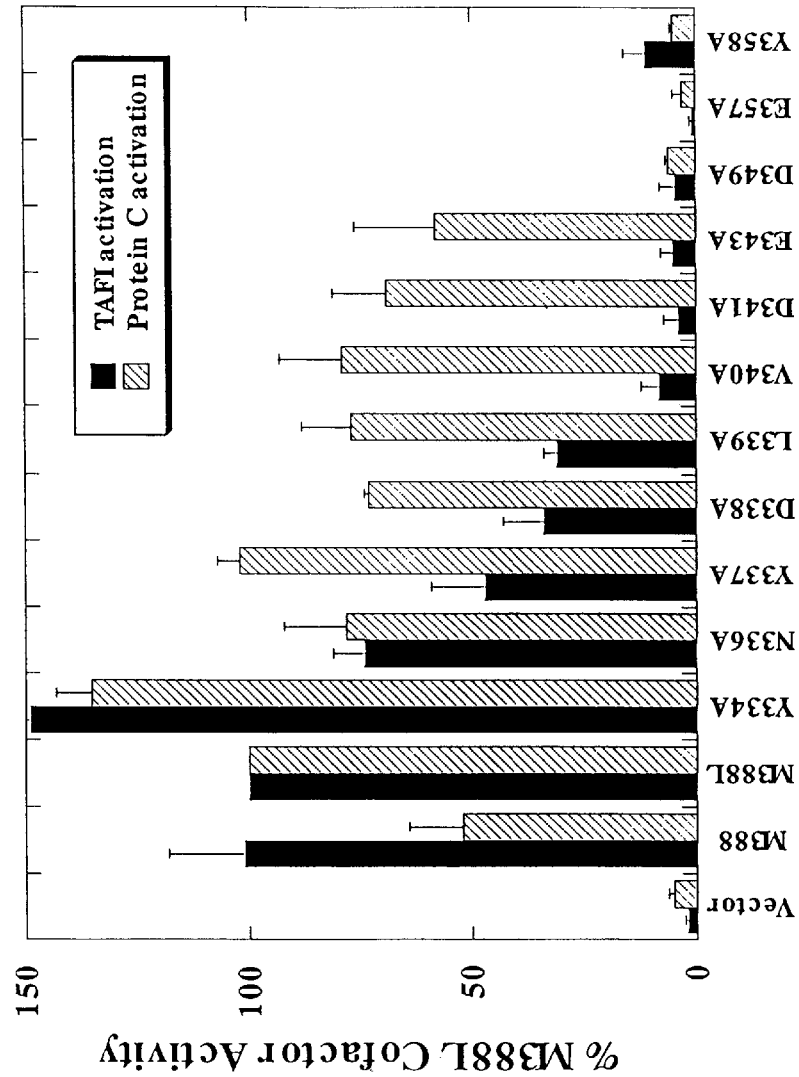

FIGURE 4

```
Met Leu Gly Val Leu Val Leu Gly Ala Leu Ala Leu Ala Gly Leu Gly
            -15              -10                -5

Phe Pro Ala Pro Ala Glu Pro Gln Pro Gly Gly Ser Gln Cys Val Glu
    -1   1              5                   10

His Asp Cys Phe Ala Leu Tyr Pro Gly Pro Ala Thr Phe Leu Asn Ala
 15              20                  25                      30

Ser Gln Ile Cys Asp Gly Leu Arg Gly His Leu Met Thr Val Arg Ser
             35                  40                   45

Ser Val Ala Ala Asp Val Ile Ser Leu Leu Asn Gly Asp Gly Gly
             50                  55                  60

Val Gly Arg Arg Arg Leu Trp Ile Gly Leu Gln Leu Pro Pro Gly Cys
         65                  70                  75

Gly Asp Pro Lys Arg Leu Gly Pro Leu Arg Gly Phe Gln Trp Val Thr
 80                  85                   90

Gly Asp Asn Asn Thr Ser Tyr Ser Arg Trp Ala Arg Leu Asp Leu Asn
 95                 100                 105                 110

Gly Ala Pro Leu Cys Gly Pro Leu Cys Val Ala Val Ser Ala Ala Glu
            115                 120                 125

Ala Thr Val Pro Ser Glu Pro Ile Trp Glu Glu Gln Gln Cys Glu Val
            130                 135                 140

Lys Ala Asp Gly Phe Leu Cys Glu Phe His Phe Pro Ala Thr Cys Arg
            145                 150                 155

Pro Leu Ala Val Glu Pro Gly Ala Ala Ala Ala Val Ser Ile Thr
    160                 165                 170

Tyr Gly Thr Pro Phe Ala Ala Arg Gly Ala Asp Phe Gln Ala Leu Pro
175                 180                 185                 190

Val Gly Ser Ser Ala Ala Val Ala Pro Leu Gly Leu Gln Leu Met Cys
            195                 200                 205

Thr Ala Pro Pro Gly Ala Val Gln Gly His Trp Ala Arg Glu Ala Pro
            210                 215                 220

Gly Ala Trp Asp Cys Ser Val Glu Asn Gly Gly Cys Glu His Ala Cys
            225                 230                 235

Asn Ala Ile Pro Gly Ala Pro Arg Cys Gln Cys Pro Ala Gly Ala Ala
            240                 245                 250

Leu Gln Ala Asp Gly Arg Ser Cys Thr Ala Ser Ala Thr Gln Ser Cys
255                 260                 265                 270
```

FIGURE 4 (con't)

```
Asn Asp Leu Cys Glu His Phe Cys Val Pro Asn Pro Asp Gln Pro Gly
                275                 280                 285

Ser Tyr Ser Cys Met Cys Glu Thr Gly Tyr Arg Leu Ala Ala Asp Gln
            290                 295                 300

His Arg Cys Glu Asp Val Asp Asp Cys Ile Leu Glu Pro Ser Pro Cys
        305                 310                 315

Pro Gln Arg Cys Val Asn Thr Gln Gly Gly Phe Glu Cys His Cys Tyr
    320                 325                 330

Pro Asn Tyr Asp Leu Val Asp Gly Glu Cys Val Glu Pro Val Asp Pro
335                 340                 345                 350

Cys Phe Arg Ala Asn Cys Glu Tyr Gln Cys Gln Pro Leu Asn Gln Thr
                355                 360                 365

Ser Tyr Leu Cys Val Cys Ala Glu Gly Phe Ala Pro Ile Pro His Glu
            370                 375                 380

Pro His Arg Cys Gln Met Phe Cys Asn Gln Thr Ala Cys Pro Ala Asp
        385                 390                 395

Cys Asp Pro Asn Thr Gln Ala Ser Cys Glu Cys Pro Glu Gly Tyr Ile
    400                 405                 410

Leu Asp Asp Gly Phe Ile Cys Thr Asp Ile Asp Glu Cys Glu Asn Gly
415                 420                 425                 430

Gly Phe Cys Ser Gly Val Cys His Asn Leu Pro Gly Thr Phe Glu Cys
                435                 440                 445

Ile Cys Gly Pro Asp Ser Ala Leu Val Arg His Ile Gly Thr Asp Cys
            450                 455                 460

Asp Ser Gly Lys Val Asp Gly Gly Asp Ser Gly Ser Gly Glu Pro Pro
            465                 470                 475

Pro Ser Pro Thr Pro Gly Ser Thr Leu Thr Pro Pro Ala Val Gly Leu
        480                 485                 490

Val His Ser Gly Leu Leu Ile Gly Ile Ser Ile Ala Ser Leu Cys Leu
495                 500                 505                 510

Val Val Ala Leu Leu Ala Leu Leu Cys His Leu Arg Lys Lys Gln Gly
                515                 520                 525

Ala Ala Arg Ala Lys Met Glu Tyr Lys Cys Ala Ala Pro Ser Lys Glu
            530                 535                 540

Val Val Leu Gln His Val Arg Thr Glu Arg Thr Pro Gln Arg Leu
            545                 550                 555
```

THROMBOMODULIN ANALOGS FOR PHARMACEUTICAL USE

This application claims the benefit of U.S. Provisional Application No. 60/213,678, filed Jun. 21, 2000, which is incorporated herein in full by reference.

FIELD OF THE INVENTION

The present invention relates to the use of analogs of thrombomodulin (TM) that have the ability to enhance the thrombin-mediated activation of protein C, but which have a significantly reduced ability to activate thrombin-activatable fibrinolysis inhibitor (TAFI), resulting in decreased clotting with an increase in fibrinolysis. These analogs are useful in, for example, antithrombotic therapy. Novel proteins, nucleic acid gene sequences, pharmaceuticals and methods of inhibiting thrombotic activity are disclosed.

BACKGROUND OF THE INVENTION

There are many disease states that would benefit from treatment with a safe and effective anticoagulant/antithrombotic. The nature of these conditions varies. For example, anticoagulant therapy is useful in acute conditions such as during thrombolytic therapy in myocardial infarction or in treatment of disseminated intravascular coagulation (DIC) associated with, for example, septicemia. Anticoagulants are also useful for less acute conditions, such as chronic use in patients that have received heart valve implants or prophylactic use in surgery patients to reduce the risk of deep venous thrombosis (DVT).

Thrombomodulin is a membrane protein that has demonstrated anticoagulant properties. In humans, it is widely distributed on the endothelium of the vasculature and lymphatics. Its physiological importance has been extensively studied. (See, for example, Esmon et al. (1982) *J. Biol. Chem.* 257:859–864, Salem et al. (1983) *J. Biol. Chem.* 259:12246–12251).

Thrombomodulin functions as a receptor for thrombin, a central enzyme in the coagulation cascade. When free, thrombin promotes coagulation both directly by converting fibrinogen to fibrin, indirectly through activation of other proteins in the coagulation cascade (Factors V, VIII and XIII, for example), and through platelet activation. When bound to thrombomodulin, however, the thrombin-thrombomodulin complex is involved in activation of protein C to activated protein C, which then downregulates the coagulation cascade by proteolytically inactivating the essential cofactors Factor Va and Factor VIIIa (Esmon et al., *Ann. N. Y. Acad. Sci.* (1991), Vol. 614, pp. 30–43) resulting in increased anticoagulant activity. The thrombin-thrombomodulin complex also is involved in activation of thrombin-activatable fibrinolysis inhibitor (TAFI), which leads to an inhibition of fibrinolysis. (See FIG. 1).

The gene encoding native thrombomodulin has been isolated and sequenced from several species, both in its genomic form and as a cDNA clone (Suzuki et al., (1987) *EMBO Journal* 6:1891–1897; Jackman et al., (1986) *Proc. Natl. Acad. Sci. USA* 83:8834–8838 and (1987) 84:6425–6429, all of which are herein incorporated by reference). Comparisons with known proteins, such as the LDL receptor, have suggested functional domains (Wen, D., et al., (1987) *Biochemistry* 26:4350–4357). One study has suggested that the fifth and sixth epidermal growth factor (EGF)-like domains have the capacity to bind thrombin (Kurosawa, S., et al., (1988) *J. Biol. Chem.* 263:5993–5996); another suggests that EGF-like domains 4, 5, and 6 are sufficient to act as a cofactor for thrombin-mediated protein C activating activity. (Zushi, et al., (1989) *J. Biol. Chem.* 264:10351–10353). More recent studies have examined the structural elements within the EGF-like domains of thrombomodulin which are required for protein C and thrombin activatable fibrinolysis factor (TAFI) activation by the thrombin-thrombomodulin complex (Kokame et al. (1998) *J. Biol. Chem.* 273:12135–12139; Wang et al. (1998) *Intl. Soc. Fibrin. Throm.* pg 11; Wang et al. (2000) *J. Biol. Chem.* 275:22942–22947). Inhibition of thrombin's direct procoagulant activity (conversion of fibrinogen to fibrin) can be attributed in part to glycosaminoglycan substituents on the thrombomodulin molecule. (Bourin, M. C. et al., (1986) *Pro. Natl. Acad. Sci. USA* 83:5924–5928). The O-linked glycosylation domain in thrombomodulin contains potential sites for the addition of these types of sulfated sugars. In addition, thrombomodulin accelerates the direct inhibition of thrombin by natural inhibitors in plasma such as protein C inhibitor (Rezaie et al., (1995) *J. Biol. Chem.* 270:25336–25339).

Soluble analogs of thrombomodulin that retain most, if not all, of the activities of the native protein have been produced. Furthermore, soluble analogs of thrombomodulin which are resistant to oxidation, resistant to proteolysis, or have in other ways been modified so as to possess a longer half-life within the circulation, have been developed (Glaser et al. These modifications have been described in U.S. Pat. No. 5,256,770 (oxidation resistance), U.S Pat. No. 5,863,760 (protease resistance), and 5,466,668 (altered glycosylation sites), all of which are incorporated herein by reference.

There is a need, however, for new and improved thrombomodulin compositions, both soluble and membrane-bound, which possess altered selectivity of the thrombin-thrombomodulin complex for the substrates protein C and TAFI, resulting in an increase in overall anticoagulant activity. Novel thrombomodulin analogs which, upon binding to thrombin, result in an increased activation of protein C and a decreased activation of TAFI as compared with native thrombomodulin, can fill this need.

SUMMARY OF THE INVENTION

In accordance with the present invention, new TM analogs, methods, and compositions are provided which can be used to treat thrombotic disease. Prior art anti-thrombotic compositions produced by recombinant techniques have been studied extensively by the present inventors, leading to improved analogs, which are described in U.S. Pat. Nos. 5,256,770, 5,863,760 and U.S. Pat. No. 5,466,668. The present invention is focused on modification of the substrate specificity of the thrombin-thrombomodulin complex produced when the novel TM analogs of the present invention are used to form this complex.

This invention provides novel TM analogs which, when bound to thrombin, result in a thrombin-thrombomodulin complex which demonstrates greater than 100% activation of protein C and less than 50% activation of TAFI as compared with native thrombomodulin (FIG. 4, SEQ ID NO: 2), the analog having amino acid substitutions at several positions within the 6 EGF-like domains of thrombomodulin, where several is defined as at least two.

Preferred embodiments of these thrombomodulin analogs are those wherein the analog has the amino acid sequence of native thrombomodulin (SEQ ID NO:2) modified at positions 340, 341, or 343 of the c-loop of the third EGF-like domain or at position 381, which is located within EGF-like domain 4, or at a combination of these positions, where the analogs are numbered in accordance with native thrombomodulin (SEQ ID NO: 2). Particularly preferred thrombomodulin analogs contain the modification H381G, combined with one of the following modifications: V340A, D341A or E343A.

A further preferred embodiment of the TM analog is a soluble analog.

A particularly preferred embodiment of the TM analog is one in which the analog is also resistant to oxidation and wherein the methionine at position 388 is replaced with leucine, wherein the analog is numbered in accordance with native thrombomodulin (SEQ ID NO: 2).

Further preferred embodiments of these TM analogs contain additional modifications to provide resistance to protease cleavage and show an altered pattern of glycosylation.

Preferred analogs are ones which contain the following modifications: removal of amino acids 1–3, H381G, M388L, R456G, H457Q, S474A, and any one of the following substitutions: V340A, D341A, or E343A.

Particularly preferred analogs are ones which contain the following modifications: removal of amino acids 1–3, H381G, M388L, R456G, H457Q, S474A, termination at P490, and any one of the following substitutions: V340A, D341A, or E343A.

This invention further provides DNA sequences encoding the TM analogs described above, as well as vectors and host cells to allow production of said TM analogs in prokaryotic or eukaryotic organisms.

This invention further provides methods for treating or preventing thrombotic disease, comprising administering an effective amount of said thrombomodulin analogs to a patient in need of anticoagulant therapy.

BRIEF DESCRIPTION OF THE DRAWINGS

FIG. 4 shows the amino acid sequence of native thrombomodulin (SEQ ID NO: 2), using the numbering system of Suzuki et al. (1987) *Embo J* 6: 1891–1897.

DETAILED DESCRIPTION OF THE INVENTION

Definitions

Figure 1:
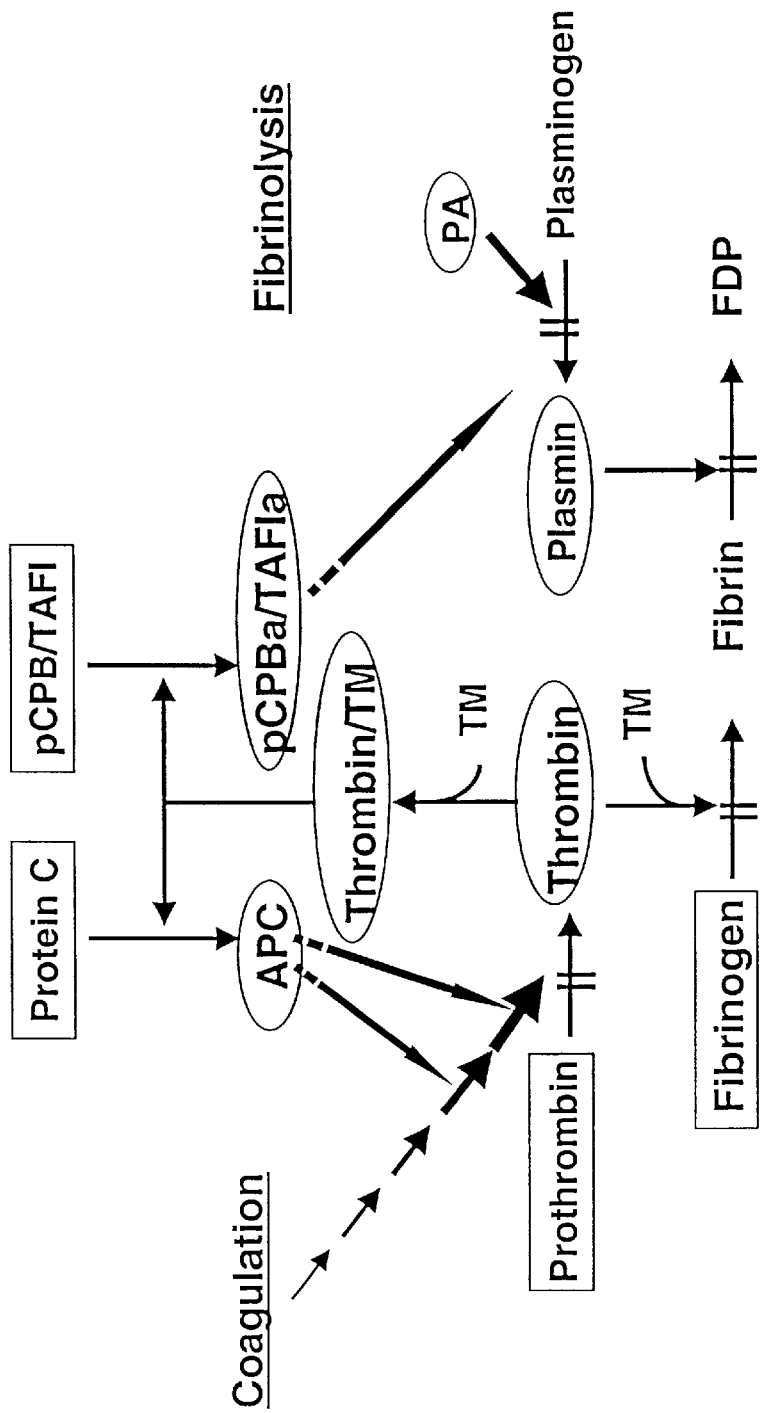
FIG. 1 shows interaction of the thrombomodulin-thrombin complex with protein C and TAFI. Abbreviations used are: APC, activated protein C; pCPB, plasma carboxypeptidase B or TAFI; pCPBa, activated plasma carboxypeptidase B; TAFIa, activated TAFI; PA, plasminogen activator; FDP, fibrin degradation peptides.
Figure 2:
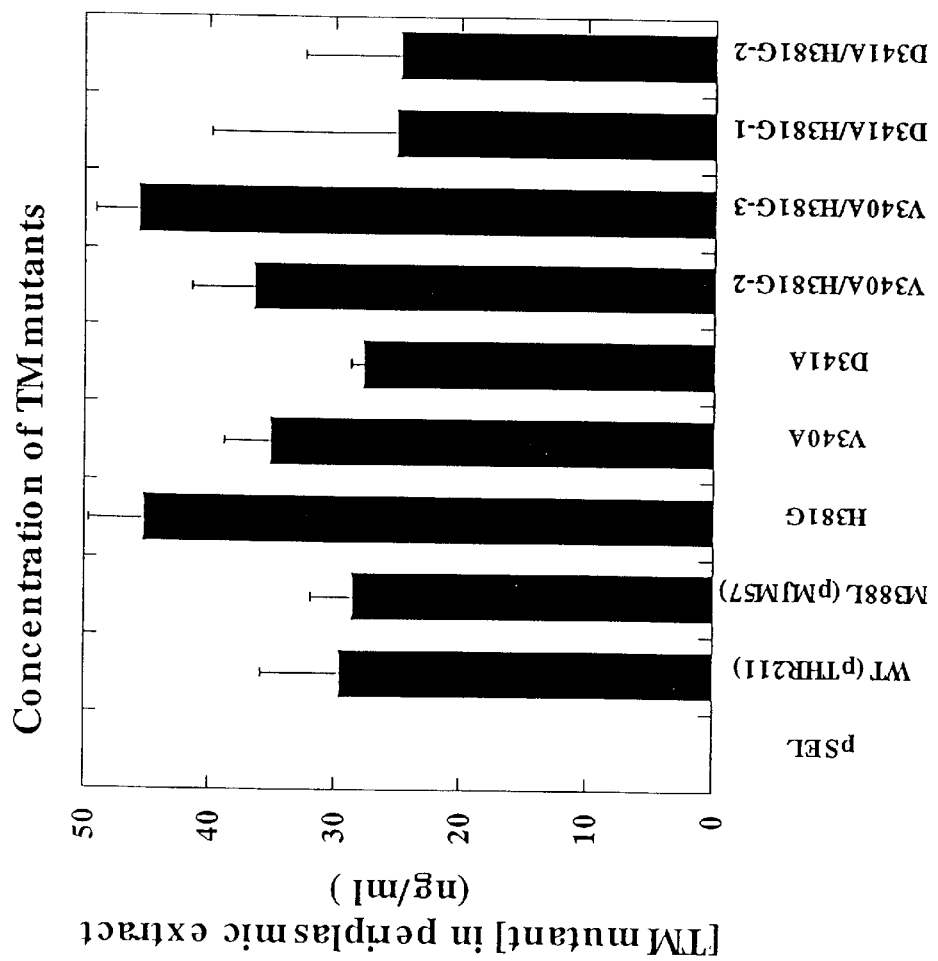
FIG. 2 shows level of TM mutants present in periplasmic extracts

As used in the specification and claims, unless specified to the contrary, the following terms have the meaning indicated:

The term "residue" refers to an amino acid that is incorporated into a peptide. The amino acid may be a naturally occurring amino acid and, unless otherwise limited, may encompass known analogs of natural amino acids that can function in a similar manner as naturally occurring amino acids. For purposes of this disclosure, amino acid residues are designated herein by their accepted three-letter or one-letter abbreviation, or by the notation "AA", which signifies the presence of an amino acid residue. The amino acids referred to herein are described by shorthand designations as follows:

TABLE 1

Amino Acid Nomenclature

| Name | 3-letter | 1 letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When describing an amino acid substitution, for purposes of this disclosure, the substitution is described by providing the amino acid present in native thrombomodulin (SEQ ID NO: 2), the location of the amino acid within the thrombomodulin sequence (using the numbering system of Suzuki et al, (1987) *EMBO J* 6:1891–1897), followed by the amino acid which has been substituted for the original: i.e. M388L refers to substitution of methionine at position 388 with leucine).

"Native thrombomodulin" refers to the full length protein as it occurs in nature (FIG. 4: SEQ ID NO: 2). Native thrombomodulin is known to contain naturally occurring polymorphisms at certain residues. For example, at position 455, there is a naturally occurring variation in the amino acid found at this position, with an alanine present 82% of the time and a valine present 18% of the time (Van der Velden et al. (1991) *Throm. Haemeostasis* 65:511–513.) For purposes of this invention, the native thrombomodulin sequence shown (FIG. 4; SEQ ID NO: 2) is one which contains valine at position 455, as described by Suzuki et al. (1987) *EMBO J* 6:1891–1897. However, all naturally occurring polymorphisms are included within the scope of the claimed analogs. When biological activities are described with reference to the native TM, the term embraces a detergent solubilized aqueous form. Often, in the context of comparison to an activity, a transfected soluble polypeptide may exhibit substantially identical properties.

"Thrombomodulin analogs" are peptides which substantially retain the biological activity of natural TM, as discussed above, and which have a molecular structure different from that of a natural version TM. For example, the term refers to proteins having an amino acid sequence identical or homologous with that of native thrombomodulin (SEQ ID NO: 2), to insoluble and soluble thrombomodulin peptides or fragments, and to oxidation resistant TM species, all having thrombomodulin-like activity. These analogs contain modifications to the native TM sequence, where such modifications can encompass substitutions, insertions, and deletions of amino acids. These analogs also include derivatives and molecules comprising amino acid changes which do not significantly decrease the protein C activation cofactor properties of the protein when compared with native TM.

The term "TM mutant" refers to a TM analog containing the designated substitution (as described above) or other indicated modification.

The terms "peptides" and "polypeptides" refer to chains of amino acids whose α carbons are linked through peptide bonds formed by a condensation reaction between the α carbon carboxyl group of one amino acid and the amino group of another amino acid. The terminal amino acid at one end of the chain (amino terminus) therefore has a free amino group, while the terminal amino acid at the other end of the chain (carboxy terminus) has a free carboxyl group.

A "protease site" refers to an amino acid or series of amino acids in a TM polypeptide which define a recognition, binding, cleavage, or other site susceptible to the activity of a protease, for example, when one or more amino acid residues encompassed by this site are substituted by another amino acid residue(s) or are deleted, the protease is no longer able to cleave the TM at that site. This term also encompasses regions of the TM molecule which are inherently susceptible to proteases, e.g., by being conformationally exposed and available to a protease activity.

A "protease cleavage site" refers to the precise location at which a protease cleaves the TM polypeptide analog.

A "single N-terminus" and "single C-terminus" have their literal meanings which functionally refer to the property of the composition, e.g., wherein, upon conventional sequential amino acid sequence analysis, each degradation cycle results in the removal of an amino acid residue which is essentially devoid of a different amino acid residue. Thus, after several cycles, e.g., 10 cycles, of stepwise removal of the N-terminal amino acids, essentially only one amino acid is recovered at each cycle. In particular, no more heterogeneity in sequence is detected than would be statistically expected from a completely pure single-chain polypeptide according to the analytic procedure used.

"Substantially retains the biological activity of native thrombomodulin" and similar terms, as used herein, means that the thrombomodulin shares biological activities with a native membrane bound TM molecule. Generally, the activity in units per milligram of protein is at least about 50%, ordinarily 75%, typically 85%, more typically 95%, preferably 100% and more preferably over 100% of the activity of native thrombomodulin (SEQ ID NO: 2). This biological activity can be that of thrombin-mediated activation of protein C (APC), of activated partial thromboplastin clotting time (aPTT), of thrombin clotting time (TCT), or of any of TM's biological, preferably therapeutic, activities. The native standard of comparison is a full-length membrane bound version of TM, but in many cases, a soluble TM comprising the lectin/EGF/O-linked domain (TM.sub.LEO) can be used as a more convenient standard.

"Glycosylation sites" refer to amino acid residues which are recognized by a eukaryotic cell as locations for the attachment of sugar residues. The amino acids where sugars are attached are typically Asn (for N-linked sugars), threonine or serine (for O-linked sugars) residues. The specific site of attachment is typically signaled by a sequence of amino acids, e.g., Asn-X-(Thr or Ser) for most N-linked attachment and (Thr or Ser)-X-X-Pro for most O-linked attachment, where X is any amino acid. The recognition sequence for glycosaminoglycans (a specific type of sulphated sugar) is generally Ser-Gly-X-Gly, but can also be X-Ser-Gly-X-Val. The terms N-linked and O-linked refer to the chemical group that serves as the attachment site between the sugar moiety and the amido acid residue. N-linked sugars are attached through an amino group; O-linked sugars are attached through an hydroxyl group.

"In vivo circulating half-life" refers to the average time it takes an administered plasma activity in a mammal to decrease by one half.

"O-linked glycosylation domain" refers to the sequence of amino acids numbered from 463 through 497 of the native thrombomodulin sequence as depicted in Table 2 (see page 10).

"Oxidation resistant analogs" refers to analogs of thrombomodulin which are able to maintain a substantial amount of biological activity after exposure to an oxidizing agent such as oxygen radicals, Chloramine T, hydrogen peroxide, or activated neutrophils.

"Pharmaceutical excipients" refers to non-toxic, medically-acceptable materials which are used to complete a medical therapeutic. These materials can be inert, such as water and salt, or biologically active, such as an antibiotic or analgesic.

"Reduced ability" refers to a statistically meaningful lowering of a biological property. The property is unlimited and the measurement or quantification of the property is by standard means.

"Sugar residues" refers to hexose and pentose carbohydrates including glucosamines and other carbohydrate derivatives and moieties which are covalently linked to a protein.

"Sulfate substituents" are sulfur-containing substituents on pentose or hexose sugars.

"Thrombin-mediated conversion of fibrinogen to fibrin" refers to the enzymatic activity by which thrombin cleaves the precursor protein fibrinogen to make fibrin monomer, which subsequently polymerizes to form a blood clot.

"Thrombotic disease" refers to a pathogenic condition in a mammal characterized by the formation of one or more thrombi that are or can be detrimental to the health of the mammal.

"Therapeutically effective amount" refers to that amount of TM analog which ameliorates the symptoms or conditions of thrombotic disease in a mammal.

"Transfer vector" refers to a vector cotransfected into another cell, e.g., an insect cell, with, e.g., a wild-type baculovirus. The transfer vector is constructed in such a way as to encourage a recombination between a viral, e.g., the baculovirus, genome and the transfer vector, e.g., replacing the baculovirus polyhedron gene with a heterologous target gene. Where a vector is being maintained by a host cell, the vector may either be stably replicated by the cells during mitosis as an autonomous structure, or is incorporated within the host's genome.

A "soluble TM analog" is a TM analog which is soluble in an aqueous solution, and typically can be secreted by a cell. For pharmacological administration, the soluble TM analog or an insoluble analog may optionally be combined with phospholipid vesicles, detergents, or other similar compounds well known to those skilled in the art of pharmacological formulation. The preferred TM analogs of the present invention are soluble in the blood stream, making the analogs useful in various anticoagulant and other therapies. The modifications which make TM soluble typically do not significantly affect many activities relative to native thrombomodulin (SEQ ID NO: 2), e.g., affinity for thrombin or activity in protein C activation.

Much of the nomenclature and general laboratory procedures referred to in this application can be found in Sambrook et.al., *Molecular Cloning, A Laboratory Manual* (2nd Ed.), Vol 1–3, Cold Spring Harbor Laboratory, Cold Spring Harbor, N.Y., 1989 or in Berger and Kimmel, *Guide to Molecular Cloning Techniques, Methods in Enzymology* 152 (Academic Press, Inc., San Diego, Calif.). The manuals are hereinafter referred to as "Sambrook" or "Berger" respectively, and are each incorporated herein by reference.

DETAILED DESCRIPTION OF THE INVENTION

Biological Activity of Thrombomodulin

The underlying pathology of thrombotic disorders is that a clot forms in response to a stimulus such as, for example, a damaged vessel wall. This stimulus triggers the coagulation cascade and thus generates thrombin which has the ability to convert fibrinogen to fibrin, the matrix of the clot. Thrombomodulin is an endothelial cell membrane protein that acts as a receptor for thrombin. In humans it is distributed on the endothelium of the blood vessels and lymphatics of all organs. Thrombin has the ability to bind reversibly to thrombomodulin. When bound to thrombomodulin, thrombin is converted from a procoagulant enzyme to an anticoagulant enzyme. The thrombin/thrombomodulin complex inhibits the coagulation cascade in at least two distinct ways. First, thrombin's binding to thrombomodulin potentiates thrombin-mediated activation of protein C, converting a zymogen to an active serine protease (Foster et al. (1985) *Proc. Natl. Acad. Sci. USA* 82: 46734677). Activated protein C proteolytically inactivates other procoagulant components of the coagulation cascade, such as Factors Va and VIIIa, which in turn inhibits the conversion of more prothrombin to thrombin. Thrombin-mediated activation of protein C is greatly enhanced when thrombin is bound to thrombomodulin, i.e., the rate of protein C activation increases at least 1000-fold. Secondly, binding to thrombomodulin has direct anticoagulant effects such as the inhibition of thrombin-mediated conversion of fibrinogen to fibrin and thrombin-mediated activation and aggregation of platelets. In addition, the thrombin-thrombomodulin complex also has antifibrinolytic effects through activation of TAFI, a plasma protein which, like protein C, is a macromolecular substrate for the thrombin-thrombomodulin complex. TAFI is activated by a single proteolytic cleavage to produce activated TAFI, a carboxypeptidase with specificity for carboxy terminal arginine and lysine residues. In fact, when it was first discovered TAFI was designated pCPB, for plasma carboxypeptidase B (see Eaton et al. (1991) *J. Biol. Chem.* 266:21833–21838; U.S. Pat. No. 5,206,161) and this was shown to be identical to the protein given the name TAFI (thrombin-activatable fibrinolysis inhibitor) by Nesheim et al. ((1995) *J. Biol. Chem.* 270:14477–14484). Activated TAFI very potently inhibits fibrinolysis.

The use of soluble thrombomodulin analogs will be effective at preventing thrombus formation, yet is safer than native thrombomodulin and other antithrombotics known in the art. The preferred thrombomodulin analogs of this invention will protect against thrombus formation when administered systemically because, once bound to thrombin, the thrombin-thrombomodulin complex formed will show increased anticoagulant activity and increased fibrinolytic activity as compared with native thrombomodulin (SEQ ID NO: 2)

Diseases in which thrombus formation plays a significant etiological role include myocardial infarction, disseminated intravascular coagulation, deep vein thrombosis, pulmonary embolism, septic shock, acute respiratory distress syndrome, unstable angina, and other arterial or venous occlusive conditions. The thrombomodulin analogs of this invention are useful in all of these, as well as in other diseases in which thrombus formation is pathological. By useful it is meant that the compounds are useful for treatment, either to prevent the disease or to prevent its progression to a more severe state. The compounds of this invention also provide a safe and effective anticoagulant, for example, in patients receiving bioprostheses, such as heart valves. These compounds may replace heparin and warfarin in the treatment of, for example, pulmonary embolism or acute myocardial infarction.

In particular these compounds would find a role in the prevention of deep vein thrombosis (DVT), for instance after surgery. The formation of blood clots in the leg is itself a non-fatal condition but is very closely tied to the development of pulmonary embolism (PE), which is difficult to diagnose and can be fatal. Despite the investigation and clinical use of several prophylactic regimens, DVT and the resulting PE remain a significant problem in many patient populations and particularly in patients undergoing orthopedic surgery. Existing prophylactic treatments such as heparin, warfarin, and dextran typically reduce the incidence of DVT in orthopedic surgery patients from more than 50% in patients at risk receiving no prophylaxis to 25–30% among treated patients. There are serious side effects, primarily bleeding complications. Currently, daily laboratory tests and adjustments in dosage are required to minimize bleeding episodes while retaining some efficacy. Based on the shortcomings of existing prophylactics, an antithrombotic which is effective at preventing DVT without predisposing the patient to bleeding could make a significant impact on patient recovery and well-being.

Angioplasty is a procedure frequently used for restoring patency in occluded arteries. Although patency may be restored, it is inherent in an angioplasty procedure that the endothelial lining of the artery is severely damaged, and blood clots frequently begin to form. Soluble thrombomodulin analogs administered in conjunction with angioplasty will prevent this deleterious side effect.

Many acute thrombotic and embolic diseases are currently treated with fibrinolytic therapy in order to remove the thrombus. The condition that has been most investigated is acute myocardial infarction (heart attack). Agents currently in use for treating acute myocardial infarction include streptokinase, tissue plasminogen activator, and urokinase. Use of these agents can lead to serious bleeding complications. Patients who have had a thrombus removed by fibrinolytic therapy and in whom the blood flow has been restored frequently suffer from reocclusion of the affected vessel, i.e., a clot reforms. Attempts have been made to prevent the reocclusions by increasing the dose or time of treatment with a thrombolytic agent, but the incidence of bleeding then increases. Thus the therapeutic index for these drugs is narrow.

Disseminated intravascular coagulation (DIC) is an acquired syndrome characterized by a systemic activation of intravascular coagulation leading to formation of microvascular thrombi in various organs and eventually contributing to the development of multiorgan failure. DIC is highly associated with a number of diseases and various clinical conditions, such as septicemia, severe trauma, malignancy and surgeries. In the early phase of DIC, the activation of coagulation is compensated by the presence of inhibitors resulting in the lack of clinical findings. However, increased plasma levels of coagulation activation markers such as thrombin-antithrombin (TAT) complexes can be detected in the laboratory analysis. In the second and third phase of DIC, the prothrombin time (PT) and the activated partial thromboplastin time (aPTT) are markedly increased while platelet count, fibrinogen concentration and inhibitor concentrations are significantly decreased. The consumption of coagulation proteins and platelets due to the ongoing coagulation may induce severe bleeding complications. Thrombomodulin analogs, especially given in the early stage of DIC, will prevent amplification of thrombin production, and consequently reduce fibrin deposition. Furthermore, TM analogs that preferentially activate protein C without concurrent activation of TAFI will result in fibrin clots that are more susceptible to removal via endogenous fibrinolysis.

The use of thrombomodulin analogs provides protection against reocclusion in part because its action is local, i.e., where thrombin is being generated or being released from a clot. Therefore, when used in combination with a thrombolytic agent whose dose can then be decreased, the risk of bleeding can be substantially reduced.

Administration of thrombomodulin analogs can be accomplished by a bolus intravenous injection, by a constant intravenous infusion, or by a combination of both routes. Also, soluble thrombomodulin mixed with appropriate excipients may be taken into the circulation from an intramuscular site. Systemic treatment with thrombomodulin analogs can be monitored by determining the activated partial thromboplastin time (aPTT) on serial samples of blood taken from the patient. The coagulation time observed in this assay is prolonged when a sufficient level of thrombomodulin is achieved in the circulation. However, this is a systemic measurement of efficacy, and the inventors have discovered that an effective dose of soluble TM analog does not necessarily affect the aPTT. As used herein, a therapeutically effective dose is defined as that level of TM analog sufficient to prevent formation of pathological clots. Dosing levels and regimens can be routinely adjusted by one of ordinary skill in the art so that an adequate concentration of thrombomodulin is maintained as measured by, for example, the activated partial thromboplastin clotting time (aPTT), the thrombin clotting time (TCT), or conversion of protein C to activated protein C (APC) assays.

Several methods are known for the detection and monitoring of thrombotic disease. Deep venous thrombosis can be detected, for example, by contrast venography, (Kerrigan, G. N. W., et al., (1974) *British Journal of Hematology* 26:469); Doppler ultrasound (Barnes, R. W. (1982) *Surgery Clinics in North America* 62:489–500); sup.125 I-labeled fibrinogen uptake scanning (Kakkar, V. V., et al., (1972) *Archives of Surgery* 104:156, Kakkar, V. V., et al., (1970) Lancet 1:540–542); impedance plethysmography (Bynum, L. J. et al., (1978) *Annals of Internal Medicine* 89:162); and thromboscintoscan (Ennis, J. T. and Elmes, R. J. (1977) Radiology 125:441). These methods are useful to monitor the efficacy of the methods and compositions described herein.

Domain Structure of TM

A DNA sequence (SEQ ID NO: 1) encoding the full-length native human thrombomodulin protein has been isolated (Suzuki, et. al., (1987) *EMBO J* 6:1891–1897, which is incorporated herein by reference). The sequence encodes a 60.3 kDa protein of 575 amino acids, which includes a signal sequence of about 18 amino acids (FIG. 4; SEQ ID NO: 2).

The sequences for bovine, mouse and human thrombomodulin exhibit a high degree of homology with one another. By analogy with other proteins, the structure of thrombomodulin can be presumptively divided into domains. The term "domain" refers to a discrete amino acid sequence that can be associated with a particular function or characteristic. Typically, a domain exhibits a characteristic tertiary structural unit. The full-length thrombomodulin gene encodes a precursor peptide containing the following domains:

TABLE 2

| TM Domains | |
|---|---|
| Approximate Amino Acid Position | Domain |
| (−18)–(−1) | Signal sequence |
| 1–226 | N-terminal domain (lectin domain; L) |
| 227–462 | 6 EGF-like domains (E) |
| 463–497 | O-linked Glycosylation (D) |
| 498–521 | Transmembrane |
| 522–557 | Cytoplasmic domain |

See C. S. Yost et al., (1983) *Cell*, 34:759–766 and D. Wen et al., (1987) *Biochemistry*, 26:4350–4357, both incorporated herein by reference.

TM Analogs With Modifications Affecting the Activity of the Thrombomodulin-thrombin Complex The binding of thrombin to thrombomodulin results in a thrombin-thrombomodulin complex whose activity is important for both activation of protein C, which ultimately inhibits blood clotting, as well as activation of a plasma carboxypeptidase named thrombin-activatable fibrinolysis inhibitor (TAFI), which is involved in the delay of clot lysis.

The structural elements within the thrombomodulin molecule which are necessary for thrombin binding, as well as activation of protein C and TAFI have been under investigation by various groups (See Kokame et al. (1998) *J. Biol. Chem.* 273:12135–12139; Wang et al. (1998) *Intl. Soc. Fibrin. Throm.* pg 11; Wang et al. (2000)*J. Biol. Chem.*275: 22942–22947). Within the six interconnected EGF-like domains contained within the thrombomodulin structure, EGF-like domains 4, 5, and 6, plus the residues connecting EGF-like domains 3 and 4, are needed for efficient protein C activation. TAFI activation requires, in addition to these structural elements, the presence of the c-loop of the third EGF-like domain (residues 333–344).

The novel compositions of the instant invention have utilized this information to produce thrombomodulin analogs, which, when bound to thrombin, result in altered activity of the thrombomodulin-thrombin complex toward the substrates, protein C and TAFI. A modification to the thrombomodulin molecule in the c-loop of the third EGF-like domain is combined with a modification to at least one residue within EGF-like domains 4–6, to produce novel compositions with altered activity toward the substrates protein C and TAFI. The modifications introduced produce thrombomodulin analogs which, when complexed with thrombin, form a thrombin-thrombomodulin complex which exhibits greater than 100% activation of protein C and less than 50% activation of TAFI as compared with a complex formed using native thrombomodulin (SEQ ID NO: 2).

A preferred modification to EGF-like domains 4–6 is H381G. Preferred modifications to the c-loop of the third EGF-like domain are V340A, D341A, or E343A.

Previous work by the inventors on thrombomodulin analogs addressed the problem of inactivation of thrombomodulin through oxidation of the TM molecule and provided for TM analogs which were oxidation resistant due to replacement of methionine at position 388 of thrombomodulin with leucine (M388L). This modification has been described in U.S. Pat. No 5,256,770, which is incorporated herein by reference.

Particularly preferred TM analog compositions are those that, in addition to modifications affecting the specificity of the thrombin-thrombomodulin complex, possess the M388L substitution which renders the analogs oxidation resistant.

Other Possible Modifications to Thrombomodulin

In addition to the modifications described above, other modifications to the native thrombomodulin (SEQ ID NO: 2) molecule may be useful to increase the therapeutic effectiveness of the thrombomodulin analogs of the present invention.

Particularly preferred TM analog compositions are those that, in addition to the modifications described above, have one or more of the following characteristics:

(i) they exhibit protease resistance, (ii) they have homogeneous N- or C-termini, (iii) they have been post-translationally modified, e.g., by glycosylation of at least some of the glycosylation sites of native thrombomodulin (SEQ ID NO: 2), (iv) they have linear double-reciprocal thrombin binding properties, (v) they are soluble in aqueous solution in relatively low amounts of detergents and typically lack a transmembrane sequence.

These modifications have been described in U.S. Pat. Nos. 5,256,770, 5,863,760, and 5,466,668, which are each incorporated herein by reference.

In particular, preferred modifications to the TM molecule which relate to these characteristics include removal of amino acids 1–3, termination at P490, and the following substitutions: R456G and H457Q (both for proteolysis resistance) and S474A (blocks glycosaminoglycan addition and slows clearance).

General Methods for Making TM Analogs

This invention embraces molecular genetic manipulations that can be achieved in a variety of known ways. The recombinant cells, plasmids, and DNA sequences of the present invention provide a means to produce pharmaceutically useful compounds wherein the compound, secreted from recombinant cells, is a soluble derivative of thrombomodulin.

Generally, the definitions of nomenclature and descriptions of general laboratory procedures used in this application can be found in J. Sambrook et al., *Molecular Cloning, A Laboratory Manual*, (1989) Cold Spring Harbor Laboratory, Cold Spring Harbor, N.Y. The manual is hereinafter referred to as Sambrook and is hereby incorporated by reference. In addition, Ausubel et al., eds., *Current Protocols in Molecular Biology*, (1987 and periodic updates) Greene Publishing Associates, Wiley-Interscience, New York, discloses methods useful in the present application.

All enzymes are used according to the manufacturer's instructions. Oligonucleotides that are not commercially available can be chemically synthesized according to the solid phase phosphoramidite triester method first described by S. L. Beaucage and M. H. Caruthers, (1981) *Tetrahedron Letts.*, 22(20):1859–1862 using an automated synthesizer, as described in D. R. Needham-VanDevanter et al., (1984) *Nucleic Acids Res.*, 12:6159–6168. Purification of oligonucleotides was by either native acrylamide gel electrophoresis or by anion-exchange HPLC as described in Pearson, J. D., and Regnier, F. E. (1983) *J. Chrom.*, 255:137–149. Nucleotide sizes are given in either kilobases (kb) or base pairs (bp). These are estimates derived from agarose or acrylamide gel electrophoresis or from published DNA sequences.

The sequence of the cloned genes and synthetic oligonucleotides can be verified using the chemical degradation method of Maxam, A. M., et al., (1980) *Methods in Enzymology*, 65:499–560, or similar methods. The sequence can be confirmed after the assembly of the oligonucleotide fragments into the double-stranded DNA sequence using the method of Maxam and Gilbert, supra, or the chain termination method for sequencing double-stranded templates of Wallace, R. B., et al., (1981) *Gene*, 16:21–26. Southern Blot hybridization techniques were carried out according to Southern et al., (1975) *J. Mol. Biol.*, 98:503.

Embodiments of this invention often involve the creation of novel peptides and genes by in vitro mutagenesis. Target genes are isolated in intermediate vectors and cloned for amplification in prokaryotes such as *E. coli*, Bacillus, or Streptomyces. Most preferred is *E. coli* because that organism is easy to culture and more fully understood than other species of prokaryotes. The Sambrook manual contains methodology sufficient to conduct all subsequently described clonings in *E coli*. Strain MH-1 is preferred unless otherwise stated. All *E. coli* strains are grown on Luria broth (LB) with glucose, or M9 medium supplemented with glucose and acid-hydrolyzed casein amino acids. Strains with resistance to antibiotics were maintained at the drug concentrations described in Sambrook. Transformations were performed according to the method described by Morrison, D. A. (1977) *J. Bact.*, 132:349–351 or by Clark-Curtiss, J. E., and Curtiss, R. (1983) *Methods in Enzymology*, 101:347–362, Eds. R. Wu et al., Academic Press, New York. Representative vectors include pBR322 and the pUC series which are available from commercial sources.

Methods by which amino acids can be removed or replaced in the sequence of a protein are well known. See, e.g., Sambrook et al., supra; Ausubel et al., supra; U.S. Pat. No. 4,737,462; U.S. Pat. No. 4,588,585; EP-0285 123; and references cited therein. Genes that encode a peptide with an altered amino acid sequence can be made synthetically, for example. A preferred method is the use of site-directed in vitro mutagenesis. Site-directed mutagenesis involves the use of a synthetic oligodeoxyribonucleotide containing a desired nucleotide substitution, insertion, or deletion designed to specifically alter the nucleotide sequence of a single-strand target DNA. Hybridization of this oligonucleotide, also called a primer, to the single-strand template and subsequent primer extension produces a heteroduplex DNA which, when replicated in a transformed cell, will encode a protein sequence with the desired mutation. Sequential rounds of site-directed mutagenesis can be used to produce analogs with multiple substitutions.

Gene Synthesis

The gene encoding native thrombomodulin (SEQ ID NO: 1) has been isolated and sequenced from several species, both in its genomic form and as a cDNA (Suzuki et al., (1987) *EMBO Journal* 6:1891–1897; Jackman, R., et al., (1986) *Proc. Natl. Acad. Sci. USA.* 83:8834–8838 and (1987) 84:6425–6429, all of which are herein incorporated by reference).

Publication of the full length DNA sequence encoding human thrombomodulin and thrombin facilitates the preparation of genes and is used as a starting point to construct DNA sequences encoding TM peptides. See, e.g., Genbank Register c/o IntelliGenetics, Inc., Mountain View, Calif. The peptides of the present invention are preferably soluble derivatives which lack the stop transfer sequence of TM in addition to having internal amino acid substitutions, although derivatives containing the stop transfer sequence are also invisioned. Furthermore, these analogs are secreted from eukaryotic cells which have been transfected or transformed with plasmids containing genes which encode these polypeptides. Methods for making modifications, such as amino acid substitutions, deletions, or the addition of signal sequences to cloned genes are known. Specific methods used herein are described below.

The full-length gene for thrombomodulin can be prepared by several methods. Human genomic libraries are commercially available. Oligonucleotide probes, specific to these genes, can be synthesized using the published gene sequence. Methods for screening genomic libraries with oligonucleotide probes are known. The publication of the gene sequence for thrombomodulin demonstrates that there are no introns within the coding region. Thus a genomic clone provides the necessary starting material to construct an expression plasmid for thrombomodulin using known methods.

A thrombomodulin encoding DNA fragment can be retrieved by taking advantage of restriction endonuclease sites which have been identified in regions which flank or are internal to the gene. (Jackman, R. W., et al., (1987) *Proc. Natl. Acad. Sci. USA.*, 84:6425–6429). Alternatively, the full length genes can also be obtained from a cDNA library. For example, messenger RNA prepared from endothelial cells provides suitable starting material for the preparation of cDNA. A cDNA molecule containing the gene encoding thrombomodulin is identified as described above. Methods for making cDNA library are well known (See Sambrook, supra).

Genes encoding TM peptides may be made from wild-type TM genes first constructed using the gene encoding full length thrombomodulin. A preferred method for producing wild-type TM peptide genes for subsequent mutation combines the use of synthetic oligonucleotide primers with polymerase extension on a mRNA or DNA template. This polymerase chain reaction (PCR) method amplifies the desired nucleotide sequence. U.S. Pat. Nos. 4,683,195 and 4,683,202 describe this method. Restriction endonuclease sites can be incorporated into the primers. Genes amplified by the PCR reaction can be purified from agarose gels and cloned into an appropriate vector. Alterations in the natural gene sequence can be introduced by the techniques of in vitro mutagenesis or by use of the polymerase chain reaction with primers that have been designed to incorporate appropriate mutations. (Innis, M. et al., eds. (1990), *PCR Protocols: A Guide to Methods and Applications*, Academic Press.) While the sequences of specific oligonucleotides used in site-directed mutagenesis to produce the TM analogs of the present invention are provided (see Example 1), one skilled in the art would be able to change the oligonucleotides to use other codons which code for the same amino acids.

The TM peptides described herein are typically secreted when expressed in eukaryotic cell culture. Secretion may be obtained by the use of the native signal sequence of the thrombomodulin gene. Alternatively, genes encoding the TM peptides of the present invention may be ligated in proper reading frame to a signal sequence other than that corresponding to the native thrombomodulin gene. For example, the signal sequence of t-PA, (see WO 89/00605 incorporated herein by reference) or of hypodermin A or B (see EP 326,419 incorporated hereby by reference) can be linked to the polypeptide (See Table 2). In one preferred embodiment of the present invention, use is made of the signal sequence of t-PA which contains the second intron of the human t-PA gene. The inclusion of the intron enhances the expression level of the adjacent structural gene.

With some analogs of this invention, those portions of the gene encoding the stop transfer and cytoplasmic domains of the carboxyl terminal region of the native thrombomodulin gene are deleted. Therefore, it is necessary to add a stop codon so that translation will be terminated at the desired position. Alternatively, a stop codon can be provided by the desired expression plasmid. Additionally, a polyadenylation sequence can be utilized to ensure proper processing of the mRNA in eukaryotic cells encoding the TM analog. Also, it may be useful to provide an initiation codon, if one is not present, for expression of the TM peptides. Such sequences may be provided from the native gene or by the expression plasmid.

Cloning vectors suitable for replication and integration in prokaryotes or eukaryotes and containing transcription and translation terminators, initiation sequences, and promoters useful for regulation of the expression of TM peptides are described herein. The vectors are comprised of expression cassettes containing at least one independent terminator sequence, sequences permitting replication of the plasmid in both eukaryotes and prokaryotes, i.e., shuttle vectors, and selection markers for both prokaryotic and eukaryotic systems.

Expression of TM Peptides in Prokaryotic Cells

In addition to the use of cloning methods in *E. coli* for amplification of cloned nucleic acid sequences it may be desirable to express TM analogs in prokaryotes. As discussed in greater detail below, the carbohydrate moieties of the mature protein are not essential for activity as a cofactor for the activation of protein C but do have an effect on the direct anticoagulant properties of the TM analogs as well as the molecule's half-life in circulation. Expression of thrombomodulin analogs in *E. coli* has provided a useful tool for analysis of this issue. It is possible to recover a therapeutically functional protein from *E. coli* transformed with an expression plasmid encoding a soluble TM analog.

Methods for the expression of cloned genes in bacteria are well known. To obtain high level expression of a cloned gene in a prokaryotic system, it is often essential to construct expression vectors which contain, at the minimum, a strong promoter to direct mRNA transcription termination. Examples of regulatory regions suitable for this purpose are the promoter and operator region of the *E. coli* beta-galactosidase gene, the *E. coli* tryptophan biosynthetic pathway, or the leftward promoter from the phage lambda. The inclusion of selection markers in DNA vectors transformed in *E. coli* are useful. Examples of such markers include the genes specifying resistance to ampicillin, tetracycline, or chloramphenicol.

See Sambrook, supra, for details concerning selection markers and promoters for use in *E. coli*. In one described embodiment of this invention, pUC19 is used as a vector for the subcloning and amplification of desired gene sequences.

Expression of TM Peptides in Eukaryotic Cells

It is expected that those of skill in the art are knowledgeable in the expression systems chosen for expression of the desired TM peptides and no attempt to describe in detail the various methods known for the expression of proteins in eukaryotes will be made.

The DNA sequence encoding a soluble TM analog can be ligated to various expression vectors for use in transforming host cell cultures. The vectors typically contain marker genes and gene sequences to initiate transcription and translation of the heterologous gene.

The vectors preferably contain a marker gene to provide a phenotypic trait for selection of transformed host cells such as dihydrofolate reductase, metallothionein, hygromycin, or neomycin phosphotransferase. The nuclear polyhedral viral protein from *Autographa californica* is useful to screen transfected insect cell lines from *Spodoptera frugiperda* and *Bombyx mori* to identify recombinants. For yeast, Leu-2, Ura-3, Trp-1, and His-3 are known selectable markers (*Gene* (1979) 8:17–24). There are numerous other markers, both known and unknown, which embody the above scientific principles, all of which would be useful as markers to detect those eukaryotic cells transfected with the vectors embraced by this invention.

Of the higher eukaryotic cell systems useful for the expression of TM analogs, there are numerous cell systems to select from. Illustrative examples of mammalian cell lines include RPMI 7932, VERO, and HeLa cells, Chinese hamster ovary (CHO) cell lines, WI38, BHK, COS-7, C127, or MDCK cell lines. A preferred mammalian cell line is CHL-1 or CHO. When CHL-1 is used, hygromycin is included as a eukaryotic selection marker. CHL-1 cells are derived from RPMI 7932 melanoma cells, a readily available human cell line. The CHL-1 cell line has been deposited with the ATCC according to the conditions of the Budapest Treaty and has been assigned #CRL 9446, deposited Jun. 18, 1987. Cells suitable for use in this invention are commercially available from the American Type Culture Collection. Illustrative insect cell lines include *Spodoptera frugiperda* (fall Armyworm) and *Bombyx mori* (silkworm).

As indicated above, the expression vector, e.g., plasmid, which is used to transform the host cell, preferably contains gene sequences to initiate the transcription, and sequences to control the translation of the TM peptide gene sequence. These sequences are referred to as expression control sequences. When the host cell is of insect or mammalian origin, illustrative expression control sequences include but are not limited to the following: the retroviral long terminal repeat promoters (1982) *Nature*, 297:479–483), SV40 promoter (1983) *Science*, 222:524–527), thymidine kinase promoter (Banerji, J., et al., (1982) *Cell*, 27:299–308), or the beta-globin promoter (Luciw, P. A., et al., (1983) *Cell*, 33:705–716). The recipient vector nucleic acid containing the expression control sequences is cleaved using restriction enzymes and adjusted in size as necessary or desirable. This segment is ligated to a DNA sequence encoding a TM peptide by means well known in the art.

When higher animal host cells are employed, polyadenylation or transcription termination sequences normally need to be incorporated into the vector. An example of a polyadenylation sequence is the polyadenylation sequence from SV40, which may also function as a transcription terminator. Genes incorporated into the appropriate vectors can be used to direct synthesis of proteins in either transient expression systems or in stable clones. In the former case yields are low, but the experiments are quick. In the latter case it takes more time to isolate high producing clones. Different vectors may be used for the two different types of experiments. In particular, in the case of transient expression, sequences may be included within the plasmid that allow the plasmid to replicate to a high copy number within the cell. These sequences may be derived from a virus such as SV40 (e.g., Doyle, C. et al., (1985) *J. Cell Biol.*, 100:704–714) or from chromosomal replicating sequences such as murine autonomous replicating sequences (Weidle et al., (1988) *Gene*, 73:427–437). The vector for use in transient expression will also often contain a strong promoter such as the SV40 early promoter (e.g., van Zonnenfeld, A. et al., (1987) *Proc. Natl. Acad. Sci. USA.*, 83:4670–4674) to control transcription of the gene of interest. While transient expression provides a rapid method for assay of gene products, the plasmid DNA is not incorporated into the host cell chromosome. Thus, use of transient expression vectors does not provide stably transfected cell lines. A description of a plasmid suitable for transient expression is provided by Aruffo, A., and Seed, B. (1987) *Proc. Natl. Acad. Sci. USA.*, 84:8573–8577.

TM analogs may alternatively be produced in the insect cell lines described above using the baculovirus system. This system has been described by Luckow, V. A., and Summers, M. D (1988) *Bio/Technology*, 6:47–55. Generally, this expression system provides for a level of expression higher than that provided by most mammalian systems. The baculovirus infects the host insect cells, replicates its genome through numerous cycles, and then produces large amounts of polyhedron crystals. The polyhedron gene can be replaced with a TM peptide gene. The polyhedron promoter will then make large amounts of analog protein following infection of the culture host cell and replication of the baculovirus genome. The non-secreted gene product is harvested from the host 3–7 days post infection. Alternatively, the TM peptide may be secreted from the cells if appropriate signal sequences are present on the protein. The host cells are competent or rendered competent for transfection by various means. There are several well-known methods of introducing DNA into animal cells. These include: calcium phosphate precipitation, DEAE-dextran technique, fusion of the recipient cells with bacterial protoplasts containing the DNA, treatment of the recipient cells with liposomes containing the DNA, electroporation, and microinjection of the DNA directly into the cells. See, Perbal, B. *"Practical Guide to Molecular Cloning,"* 2nd edition, John Wiley & Sons, New York and Wigler, et al., (1987) *Cell*, 16:777–785, which are each incorporated herein by reference.

Culturing Cells

It is preferred that the host cell is capable of rapid cell culture and able to appropriately glycosylate expressed gene products. Cells known to be suitable for dense growth in tissue culture are particularly desirable and a variety of invertebrate or vertebrate cells, both normal and transformed, have been employed in the art. In particular, cells which are suitable hosts for recombinant TM expression and which produce or contain, under culturing conditions, a protease which results in the cleavage of native thrombomodulin now pose no problem in cleaving the mutated protease insensitive TM analog. Examples of such cells include CHO, CHL-1 (characterized as a human melanoma cell), Sf9 cells, etc., which are publicly available from the ATCC.

The transfected cells are grown up by means well known in the art. For examples, see Kuchler et al. (1977) *Biochemi-* cal *Methods in Cell Culture and Virology*. The expression products are harvested from the cell medium in those systems where the protein is secreted from the host cell or from the cell suspension after disruption of the host cell system by, e.g., mechanical or enzymatic means, which are well known in the art.

Purification of TM Analogs

It is preferred that the TM peptides of this invention be secreted by cultured recombinant eukaryotic cells. The TM analogs are produced in serum-free or serum supplemented media and are secreted intact. If prokaryotic cells are used, the TM analogs may be deposited intracellularly. The peptides may be fully or partially glycosylated or non-glycosylated. Following the growth of the recombinant cells and concomitant secretion of TM analogs into the culture media, this "conditioned media" is harvested. The conditioned media is then clarified by centrifugation or filtration to remove cells and cell debris. The proteins contained in the clarified media are concentrated by adsorption to any suitable resin such as, for example, Q Sepharose or metal chelators, or by use of ammonium sulfate fractionation, polyethylene glycol precipitation, or by ultrafiltration. Other means known in the art may be equally suitable. Further purification of the TM analogs can be accomplished in the manner described in Galvin, J. B., et al., (1987) *J. Biol. Chem.*, 262:2199–2205 and Salem, H. H. et al., (1984) *J. Biol. Chem.*, 259:12246–12251 and in the manner described in the embodiment disclosed herein. The purification of TM analogs secreted by cultured cells may require the additional use of, for example, affinity chromatography, ion exchange chromatography, sizing chromatography, or other conventional protein purification techniques. See, e.g., Deutscher (ed.), "Guide to Protein Purification" in *Methods in Enzymology*, Vol. 182 (1990).

Recombinant TM analogs may be found in different forms which are distinguishable under nonreducing chromatographic conditions. Removal of those species having a low specific activity is desirable and is achieved by a variety of chromatographic techniques including anion exchange or size exclusion chromatography. Recombinant TM analogs may be concentrated by pressure dialysis and buffer exchanged directly into volatile buffers (e.g., N-ethylmorpholine (NEM), ammonium bicarbonate, ammonium acetate, and pyridine acetate). In addition, samples can be directly freeze-dried from such volatile buffers resulting in a stable protein powder devoid of salt and detergents. In addition, freeze-dried samples of recombinant analogs can be efficiently resolubilized before use in buffers compatible with infusion (e.g., phosphate buffered saline). Other suitable salts or buffers might include hydrochloride, hydrobromide, sulfate, acetate, benzoate, malate, citrate, glycine, glutamate, and aspartate.

Laboratory Assays for Measuring TM Activity

A number of laboratory assays for measuring TM activity are available. Protein C cofactor activity can be measured in the assay described by Salem, et al., (1984) *J. Biol. Chem.* 259(19):12246–12251 and Galvin, et al., (1987) *J. Biol. Chem.* 262(5):2199–2205. In brief, this assay consists of two steps. The first is the incubation of the test TM analog with thrombin and protein C under defined conditions (see Examples below). In the second step, the thrombin is inactivated with hirudin or antithrombin III and heparin, and the activity of the newly activated protein C is determined by the use of a chromogenic substrate, whereby the chromophore is released by the proteolytic activity of activated protein C. This assay is carried out with purified reagents.

Alternatively the effect of a TM analog can be measured using plasma in clotting time assays such as the activated partial thromboplastin time (aPTT), thrombin clotting time (TCT), and/or prothrombin time (PT). The aPTT assay is dependent on both the activating of protein C, as well as the direct inhibition of thrombin, while the TCT and PT assays are dependent only on the inhibition of thrombin. Prolongation of the clotting time in any one of these assays demonstrates that the molecule can inhibit coagulation in plasma. Assays can be run on an automatic coagulation timer according to the manufacturer's specifications; Medical Laboratory Automation Inc. distributed by American Scientific Products, McGaw Park, III. (See also H. H. Salem et al., (1984) *J. Biol. Chem.*, 259:12246–12251, which is incorporated herein by reference).

TAFI activation can be measured as described by Wang et al. ((2000) *J. Biol. Chem.*), utilizing the fact that activated TAFI is a carboxypeptidase. In this assay, extracts containing the TM analog in question are incubated with thrombin, and the mixture then incubated with purified TAFI. The amount of activated TAFI produced is determined by the use of a chromogenic substrate, whereby the chromophore is released by the proteolytic action of activated TAFI (see Example 2). Alternatively, TAFI activation can be assayed by a plasma clot lysis assay either in a defined system using purified proteins or in a plasma milieu (Nagashima et al. (2000) *Throm. Research* 98:333–342).

The assays described above are used to identify soluble TM analogs that are able to bind thrombin and to assess the ability of the thrombin-thrombomodulin complex formed with these analogs to either activate protein C or TAFI, both in purified systems and in a plasma milieu. Further assays can be used to evaluate other activities of native thrombomodulin such as inhibition of thrombin catalyzed formation of fibrin from fibrinogen (Jakubowski, et al., (1986) *J. Biol. Chem.* 261(8):3876–3882), inhibition of thrombin activation of Factor V (Esmon, et al., (1982) *J. Biol. Chem.* 257:7944–7947), accelerated inhibition of thrombin by antithrombin III and heparin cofactor 11 (Esmon, et al., (1983) *J. Biol. Chem.* 258:12238–12242), inhibition of thrombin activation of Factor XIII (Polgar, et al., (1987) *Thromb. Haemostas.* 58:140), inhibition of thrombin mediated inactivation of protein S (Thompson and Salem, (1986) *J. Clin. Inv.* 78(1):13–17) and inhibition of thrombin mediated platelet activation and aggregation (Esmon, et al., (1983) *J. Biol. Chem.* 258:12238–12242).

Formulation and Use of Thrombomodulin Analogs

The soluble TM analogs described herein may be prepared in a lyophilized or liquid formulation. The material is to be provided in a concentration suitable for pharmaceutical use as either an injectable or intravenous preparation.

These analogs can be administered alone or as mixtures with other physiologically acceptable active materials, such as antibiotics, other anticoagulants, one-chain t-PA, or inactive materials, or with suitable carriers such as, for example, water or normal saline. The analogs can be administered parenterally, for example, by injection. Injection can be subcutaneous, intravenous or intramuscular. These analogs are administered in pharmaceutically effective amounts and often as pharmaceutically acceptable salts, such as acid addition salts. Such salts can include, e.g., hydrochloride, hydrobromide, phosphate, sulphate, acetate, benzoate, malate, citrate, glycine, glutamate, and aspartate, among others. See, e.g., *Remington's Pharmaceutical Sciences* (17th ed.), Mack Publishing Company, Easton, Pa., and Goodman & Gilman's, *The Pharmacological Bases of Therapeutics*, 8th ed., Pergamon Press, 1985, both of which are herein incorporated by reference. The analogs described herein may display enhanced in vivo activity by incorporation into micelles and/or phospholipid aggregates. Methods for incorporation into ionic detergent aggregates or phospholipid micelles are known.

An antithrombotic agent can be prepared using the soluble TM analogs described herein and can consist of a completely purified analog alone or in combination with a thrombolytic agent as described above. Analogs of the present invention which are shown to have the above recited physiological effects can find use in numerous therapeutic applications such as, for example, the inhibition of blood clot formation. Thus, these compounds can find use as therapeutic agents in the treatment of various circulatory disorders, such as, for example, coronary or pulmonary embolism, strokes, as well as the prevention of reocclusion following thrombolytic therapy, and these compounds have utility in the cessation of further enlargement of a clot during an infarction incident. Further, the analogs disclosed can be useful for treatment of systemic coagulation disorders such as disseminated intravascular coagulation (DIC), which is often associated with septicemia, certain cancers, and toxemia of pregnancy.

These analogs can be administered to mammals for veterinary use, such as with domestic animals, and for clinical use in humans in a manner similar to other therapeutic agents, that is, in a physiologically acceptable carrier. In general, the administration dosage for the TM analog will range from about at least 0.0002 μg/kg, more usually 0.02 μg/kg, and less than 5000 μg/kg, usually less than 2000 μg/kg, more usually less than 500 μg/kg, usually 0.02 to 2000 μg/kg and more usually 0.02 to 500 μg/kg of the host body weight. These dosages can be administered by constant infusion over an extended period of time, until a desired circulating level has been attained, or preferably as a bolus injection. Optimal dosages for a particular patient can routinely be determined by one of ordinary skill in the art.

Gene Therapy

The thrombomodulin analogs of the present invention may be employed in accordance with the present invention by expression of such polypeptides in vitro and in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, Lenti virus, Myeloproliferative Sarcoma Virus, and mammary tumor virus. In one embodiment, the retroviral plasmid vector is derived from Moloney Murine Leukemia Virus.

Viruses other than retroviruses may also be used to deliver selected TM polynucleotides; i.e. the DNA viruses, such as adenovirus and adenoassociated virus and Herpes virus, and derivatives thereof. Plasmids containing the nucleotide sequences of interest may also be delivered in complexes with lipids or lipid derivatives and in complexes with a variety of other biochemical and chemical reagents that are known to facilitate delivery of polynucleotides into cells in vitro or in vivo.

Such vectors will include one or more promoters for expressing the polypeptide. Suitable promoters which may be employed include, but are not limited to, the retroviral LTR; the SV40 promoter; and the human cytomegalovirus (CMV) promoter (Miller et al., *Biotechniques* 7: 980–990, 1989), or any other promoter (e.g., cellular promoters such as eukaryotic cellular promoters including, but not limited to, the histone, RNA polymerase III, and β actin promoters). Other viral promoters which may be employed include, but are not limited to, adenovirus promoters, thymidine kinase (TK) promoters, and B19 parvovirus promoters. The promoter also may be the native promoter which controls the gene encoding the polypeptide. The selection of a suitable promoter will be apparent to those skilled in the art from the teachings contained herein.

The retroviral plasmid vector is employed to transduce packaging cell lines to form producer cell lines. Examples of packaging cells which may be transfected include, but are not limited to, the PE5OI, PA317 Y-2, Y-AM, PAI2, T19-14X, VT-19-17-H2, YCRE, YCRIP, GP+E-86, GP+envAml2, and Dan cell lines as described in Miller, A., *Human Gene Therapy* 1: 5–14, 1990. The vector may be transduced into the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line will generate infectious retroviral vector particles, which include the polynucleotide sequence(s) encoding the polypeptides. Such retroviral vector particles then may be employed to transduce eukaryotic cells, either in vitro or in vivo. The transduced eukaryotic cells will express the polynucleotide(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. Viral and non-viral vectors of the kind described above may be used to deliver polynucleotide sequences which encode the thrombomodulin analog of choice. The polynucleotides may code for full-length thrombomodulin analog mRNA or fragments thereof. Delivery of such polynucleotide sequences to patients following bypass surgery could serve to protect the endothelium by preventing coagulation as well as preventing accelerated atherosclerosis at graft sites.

Without further elaboration, it is believed that one skilled in the art can,using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight. The entire disclosures of all applications, patents, and publications, cited above and below, are hereby incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

EXAMPLE 1

Isolation and Expression of TM Analog Sequences

Cloning Genes for producing recombinant thrombomodulin analog peptides were isolated as described in U.S. Pat. Nos. 5,256,770 and 5,466,668, each herein incorporated by reference. Briefly, human DNA was used to isolate a gene encoding the 6-EGF-like domains of thrombomodulin corresponding to amino acids 227–462, as well as other portions of the thrombomodulin peptide (See Table 2). This DNA was isolated from fetal liver according to the method of Blin, N. and Stafford, D. W. ((1976) *Nucleic Acids Res.* 3:2303–2308). The DNA was then used as a template in a polymerase chain reaction with synthetically derived primers selected to embrace the desired regions. See e.g., Innis et al., (1990) *PCR Protocol, A Guide to Methods and Applications*, Academic Press.

Isolation of genes encoding amino acids 227–462. The following steps provide a means to obtain a DNA insert encoding amino acid 227–462 and uses primers #1034 (5'CCGGGATCCTCAACAGTCGGTGCCAATGTGGCG3') (SEQ ID NO: 3) and #1033 (5'CCGGGATCCTGCAGCGTGGAGAACGGCGGCTGC3') (SEQ ID NO: 4). It is understood that by modifying the procedures set forth below by using alternative primers, other soluble TM analogs can be obtained.

The sequence of the #1034 and #1033 primers correspond to the 5' and 3' ends of the desired domain (6 EGF-like domains), but they have been modified so that they contain a BamHI site. A terminal codon (TGA) was introduced following base 1590. The polymerase chain reaction was run under the conditions described by Saiki, et al., (1988) *Science* 320:1350–1354, except that the initial temperature of annealing was 37° C. After 10 cycles, the annealing temperature was raised to 45° C. for the remaining 30 cycles. An aliquot of the reaction products was separated on a 5% polyacrylamide gel and visulaized by ethidium bromide staining. A band of the predicted size (700 bp) could clearly be seen. Alternatively one can sequence this band or hybridize it to an internal probe to confirm its identity.

This fragment, through a series of intermediate constructs, was placed under the control of the β-lactamase promoter and signal sequence in pKT279. An EcoR5-Bgl2 fragment of the result ant plasmid and a ScaI-SacI fragment of pGEM-3Zf DNA containing the f1 origin of replication were then inserted into pSELECT-1 vector at EcoR5-BamHI and ScaI-SacI sites, respectively, to construct an *E. coli* expression vector, pTHR211, coding for a TM analog containing the 6-EGF-like domains ($TM_E$). Plasmid pTHR211 was used to generate plasmid pMJM57 containing a leucine substitution for the methionine at position 388 (M388L), using site-directed mutagenesis as described below.

Site-directed mutagenesis Plasmids coding for TM mutants were constructed using site-directed mutagenesis either as described by Kunkel et al. ((1987) *Methods in Enzym.* 154:367–382) or as described in the protocol for QuikChange™ site-directed mutagenesis kit (Stratagene, LaJolla, Calif.). In the first protocol, a single-stranded uracil DNA template, prepared from *E. coli* strain CJ236 with R408 helper phage, was used for synthesis of the mutagenic strand in the presence of specific oligonucleotides with T4 DNA polymerase and T4 DNA ligase. The specific oligonucleotides used are listed below (all given in the 5' to 3' direction).

for M388L: CCC CAC GAG CCG CAC AGG TGC CAG CTG TTT TGC MC CAG ACT GCC TGT CCA GCC G (SEQ ID NO: 5);

for Y334A: CGA GTG CCA CTG TGC ACC TAA CTA CGA C (SEQ ID NO: 6);

for N336A: CAC TGC TAC CCT GCA TAT GAC CTG GTG GAC (SEQ ID NO: 7);

for Y337A: CCA CTG CTA CCC GAA TGC CGA CCT GGT GGA (SEQ ID NO: 8);

for D338A: CTA CCC TAA CTA TGC ATT GGT GGA CGG CG (SEQ ID NO: 9);

for L339A: CCT AAC TAC GAC GCG GTC GAC GGC GAG TGT (SEQ ID NO: 10);

for V340A: ACT ACG ACC TGG CGG ACG GCG AMT GCG TGG AGC CCG TG (SEQ ID NO: 11);

for D341A: ACG ACC TGG TGG CCG GCG AAT GCG TGG AGC CCG TG (SEQ ID NO: 12);

for E343A: TGG TGG ACG GCG CAT GCG TGG AGC CCG TG (SEQ ID NO: 13);

for D349A: GGC GAG TGT GTG GAG CCC GTG GCG CCG TGC TTC AGA GCC MC TGC G (SEQ ID NO: 14);

for E357A: CCC GTG CTT CAG AGC CAA CTG CGC ATA CCA GTG CCA GCC CCT GM CC (SEQ ID NO: 15);

for Y358A: GCC AAC TGC GAG GCC AG TGT CAA CCC CTG AAC CAA (SEQ ID NO: 16).

A restriction enzyme recognition site was incorporated into each oligonucleotide without changing the amino acid sequence, and the resultant transformants were characterized by restriction enzyme digestion, followed by DNA sequence confirmation.

In the second method, a double-stranded DNA was used as a template in the polymerase chain reaction (PCR) in the presence of specific oligonucleotides according to the manufacturer's specifications. The primers used to produce H381G were 5'GCG CCC ATT CCC GGC GAG CCG CAC AG3' (SEQ ID NO: 17)and 5'CTG TGC GGC TCG CCG GGA ATG GGC GC3' (SEQ ID NO: 18). The PCR products were digested with a restriction enzyme, Dpn1, and transformed into competent DH5α cells. The transformants were characterized by DNA sequence analysis.

Analogs containing multiple sequence modifications were produced using the methods described in a sequential manner. Following the first round of mutagenesis and DNA sequence analysis, the once-modified DNA was used as a template for the next round of mutagenesis.

Preparation of Periplasmic Extracts DH5α cells expressing TM mutants were grown to saturation in 1.5 ml of L-broth containing ampicillin (50 μg/ml) at 37° C. Cells were harvested by centrifuging at 14,000 rpm in a microcentrifuge for 25 s and washed once with 0.5 ml of 100 mM Tris-HCl, pH 8.0, 50 mM NaCl. Cells were suspended for 10 min at room temperature in 0.5 ml of 300 mM Tris-HCl, pH 8.0, 20% sucrose, 1 mM EDTA, 0.5 mM $MgCl_2$. Cells were centrifuged as before and resuspended in 0.15 ml of ice-cold 0.5 mM $MgCl_2$ for 10 min. Periplasmic extracts were collected by centrifugation.

EXAMPLE 2

TM Activity Assays

Protein C Activation. All reagents were diluted in 2.5 mM $CaCl_2$ 100 mM NaCl, 5 mg/ml BSA, 20 mM Tris-HCl, pH 7.4. Fifteen μl of each periplasmic extract was incubated with protein C (1 μM final) and thrombin (3.6 nM final) for 1 hr at 37° C. Excess hirudin (2 U/ml final) was added to stop the activation. After 5 minutes at 37° C., a chromogenic substrate, S-2266 (0.5 mM final) was added and the rate of increase in absorbance at 405 nm (mOD/min) was measured using a Vmax Kinetic Microplate Reader and Softmax programs (Molecular Devices, Menlo Park, Calif.).

TAFI Activation Assay For the activation of TAFI, a 20 ul aliquot of periplasmic extract from each mutant was preincubated with thrombin (13 nM final) in 20 mM HEPES, pH 7.5/150 mM NaCl/5mM $CaCl_2$ for 5 minutes at room temperature. The mixtures were them incubated with purified recombinant TAFI (18 nM final) and a substrate, hippuryl-arginine (1.0 mM final) in a total volume of 60 ul for 60 minutes. The amount of activated TAFI was quantitated by measuring the hydrolysis of hippuryl-arginine to hippuric acid, followed by conversion of hippuric acid to a chromogen with 80 μl phosphate buffer (0.2 M, pH 8.3) and 60 ul 3% cyanuric chloride in dioxane (w/v). After thorough mixing, absorbance of the clear supernatant was measured at 382 nm. The amount of thrombin-dependent activation of TAFI was calculated by subtracting the background absorbance produced in the absence of thrombin for each mutant.

Figure 3A:
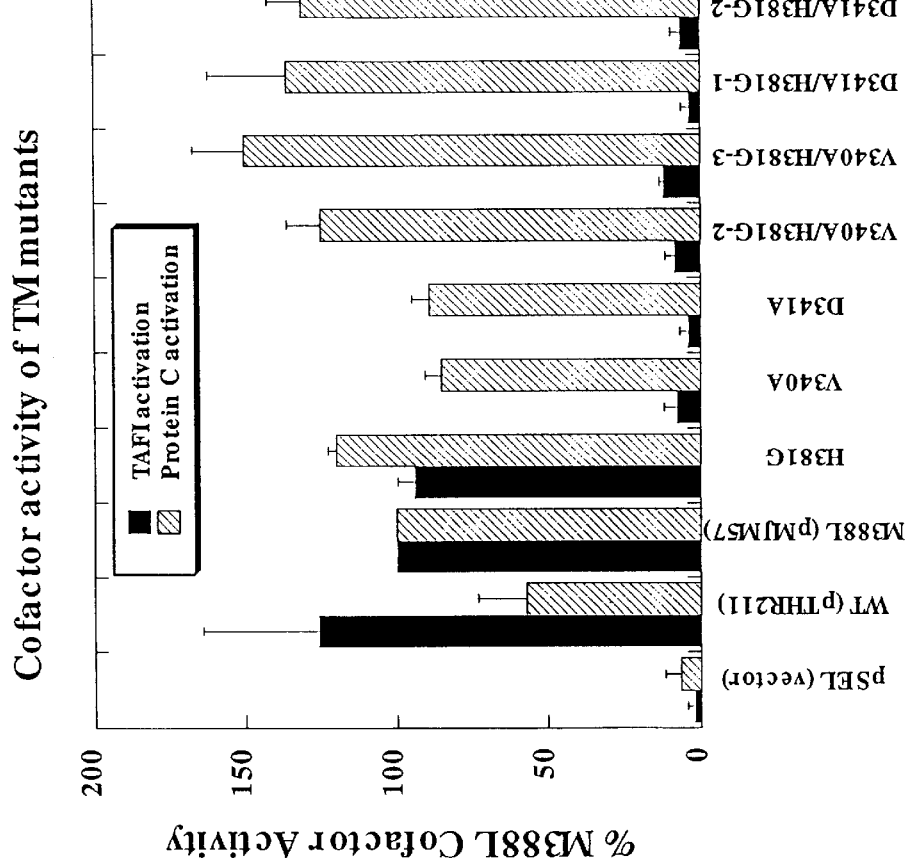
FIG. 3 (A and B) shows cofactor activity of periplasmic extracts of thrombomodulin mutants for thrombin catalyzed activation of protein C and TAFI.

Assays for both Protein C and TAFI activation contained extracts of DH5α cells transfected with either pSelect-1 vector (no $TM_E$), wild-type ($TM_E$M388 (pTHR211), or $TM_E$M388L(pMJM57) as internal controls. Cofactor activities of $TM_E$(M388L) alanine mutants were expressed as percentages of the activity of $TM_E$(M388L). Each TM mutant was assayed for both protein C and TAFI activation in duplicate using three independent preparations of extracts. (see FIG. 3).

EXAMPLE 3

TM Analog Antigen Determination

Mouse monoclonal antibodies 43B and 531 were produced according to the procedure of Esmon et al. (1987) Dev. Biol. Stand. 67:75–82), following immunization with $TM_E$(Sf9)WT (Clarke et al. (1993) J. Biol. Chem. 268: 6309–6315). Dynatech Immulon 4 microtiter plates were coated with anti-TM monoclonal 43B; 100 μl of 7.5 μg/ml 43B in 0.1 M MOPS, 150 mM NaCl, 5 mM $CaCl_2$, pH 7 were added to each well and incubated overnight at 4° C. Plates were then washed five times with PBST (PBS+0.05% Tween 20, v/v), blocked with 200 μl of 0.1% BSA in PBST/well for 2 hr at 37° C., and washed as above. TM standard ($TM_E$(Sf9)WT) or unknowns in the range of 3–30 ng/ml were added in 100 μl of 0.1% BSA in PBST, incubated 1 hr at 37° C., and washed as above. Biotinylated anti-TM 531, 100 μl of 500 ng/ml in 0.1% BSA in PBST/well, was incubated for 1 hr at 37° C. and washed. Streptavidin-alkaline phosphatase (100 μl of 0.3 μg/ml) containing 0.1% BSA in PBST was added and incubated for 1 hr at 37° C. and washed. P-Nitrophenyl phosphate substrate was added at 1 mg/ml in substrate buffer (Zymed Laboratories Inc., South San Francisco, Calif.), 100 μl/well, and incubated 30 min at room temperature. The plate was read on a microtiter plate reader at 405 nm.

What is claimed is:

1. A thrombomodulin analog, wherein the amino acid sequence of native thrombomodulin (SEQ ID NO: 2) is modified at positions 340, 341, or 343 and at position 381, and wherein the modified analog has greater than 100% of the ability to potentiate thrombin-mediated activation of protein C and less than 50% of the ability to potentiate thrombin-mediated activation of TAFI, as compared with native thrombomodulin (SEQ ID NO: 2).

2. The modified thrombomodulin analog of claim 1, wherein the valine at position 340 of the thrombomodulin analog is replaced with an alanine and wherein the histidine at position 381 of the thrombomodulin analog is replaced with a glycine.

3. The modified thrombomodulin analog of claim 1, wherein the aspartic acid at position 341 of the thrombomodulin analog is replaced with an alanine and wherein the histidine at position 381 of the thrombomodulin analog is replaced with a glycine.

4. The modified thrombomodulin analog of claim 1, wherein the glutamic acid at position 343 of the thrombomodulin analog is replaced with an alanine and wherein the histidine at position 381 of the thrombomodulin analog is replaced with a glycine.

5. The modified thrombomodulin analog of claim 1, wherein the analog is soluble.

6. The modified thrombomodulin analog of claim 1, wherein the modified analog is made resistant to oxidation by the substitution of the methionine at position 388 with a leucine.

7. The modified thrombomodulin analog of claim 1, wherein the analog is modified in the sugar residues of the O-linked glycosylation domain of native thrombomodulin (SEQ ID NO: 2).

8. The modified thrombomodulin analog of claim 7, wherein the analog is modified such that the O-linked glycosylation domain has no chondroitin sulfate.

9. The modified thrombomodulin analog of claim 1, wherein the modified analog is made resistant to protease cleavage by the substitution of the amino acids at positions 456 and 457 of native thrombomodulin (SEQ ID NO: 2).

10. The modified thrombomodulin analog of claim 1, wherein the amino acid sequence of native thrombomodulin (SEQ ID NO: 2) is modified at the following positions:
   removal of amino acids 1–3,
   V340A,
   H381G,
   M388L,
   R456G,
   H457Q, and
   S474A.

11. The modified thrombomodulin analog of claim 1, wherein the amino acid sequence of native thrombomodulin (SEQ ID NO: 2) is modified at the following positions:
   removal of amino acid 1–3,
   D341A,
   H381G,
   M388L,
   R456G,
   H457Q, and
   S474A.

12. The modified thrombomodulin analog of claim 1, wherein the amino acid sequence of native thrombomodulin (SEQ ID NO: 2) is modified at the following positions:
   removal of amino acid 1–3,
   E343A,
   H381G,
   M388L,
   R456G,
   H457Q, and
   S474A.

13. The modified thrombomodulin analog of claim 1, wherein the amino acid sequence of native thrombomodulin (SEQ ID NO: 2) is modified at the following positions:

removal of amino acids 1–3,
V340A,
H381G,
M388L,
R456G,
H457Q,
S474A, and
terminating at P490.

14. The modified thrombomodulin analog of claim 1, wherein the amino acid sequence of native thrombomodulin (SEQ ID NO: 2) is modified at the following positions:
removal of amino acid 1–3,
D341A,
H381G,
M388L,
R456G,
H457Q,
S474A, and
terminating at P490.

15. The modified thrombomodulin analog of claim 1, wherein the amino acid sequence of native thrombomodulin (SEQ ID NO: 2) is modified at the following positions:
removal of amino acid 1–3,
E343A,
H381G,
M388L,
R456G,
H457Q,
S474A, and terminating at P490.

16. A sterile composition useful for treating a thrombotic disease or condition in mammals, comprising a therapeutically effective dose of a purified thrombomodulin analog, wherein the amino acid sequence of native thrombomodulin (SEQ ID NO: 2) is modified at positions 340, 341, or 343 and at position 381, and wherein the modified analog has greater than 100% of the ability to potentiate thrombin-mediated activation of protein C and less than 50% of the ability to potentiate thrombin-mediated activation of TAFI, as compared with native thrombomodulin (SEQ ID NO: 2).

* * * * *

SEQUENCE LISTING

```
<160> NUMBER OF SEQ ID NOS: 18

<210> SEQ ID NO 1
<211> LENGTH: 3466
<212> TYPE: DNA
<213> ORGANISM: Homo sapiens
<220> FEATURE:
<221> NAME/KEY: CDS
<222> LOCATION: (151)..(1875)
<223> OTHER INFORMATION:
<220> FEATURE:
<221> NAME/KEY: mat_peptide
<222> LOCATION: (205)..()
<223> OTHER INFORMATION:

<400> SEQUENCE: 1
caggggctgc gcgcagcggc aagaagtgtc tgggctggga cggacaggag aggctgtcgc      60
catcggcgtc ctgtgcccct ctgctccggc acggccctgt cgcagtgccc gcgctttccc     120
```

```
cggcgcctgc acgcggcgcg cctgggtaac atg ctt ggg gtc ctg gtc ctt ggc      174
                                Met Leu Gly Val Leu Val Leu Gly
                                    -15 gcg ctg gcc ctg gcc ggc ctg ggg ttc ccc gca ccc gca gag ccg cag      222
Ala Leu Ala Leu Ala Gly Leu Gly Phe Pro Ala Pro Ala Glu Pro Gln
-10              -5              -1  1               5 ccg ggt ggc agc cag tgc gtc gag cac gac tgc ttc gcg ctc tac ccg      270
Pro Gly Gly Ser Gln Cys Val Glu His Asp Cys Phe Ala Leu Tyr Pro
            10              15                  20 ggc ccc gcg acc ttc ctc aat gcc agt cag atc tgc gac gga ctg cgg      318
Gly Pro Ala Thr Phe Leu Asn Ala Ser Gln Ile Cys Asp Gly Leu Arg
        25              30              35 ggc cac cta atg aca gtg cgc tcc tcg gtg gct gcc gat gtc att tcc      366
Gly His Leu Met Thr Val Arg Ser Ser Val Ala Ala Asp Val Ile Ser
    40              45              50 ttg cta ctg aac ggc gac ggc ggc gtt ggc cgc cgg cgc ctc tgg atc      414
Leu Leu Leu Asn Gly Asp Gly Gly Val Gly Arg Arg Arg Leu Trp Ile
55              60              65              70 ggc ctg cag ctg cca ccc ggc tgc ggc gac ccc aag cgc ctc ggg ccc      462
Gly Leu Gln Leu Pro Pro Gly Cys Gly Asp Pro Lys Arg Leu Gly Pro
            75              80              85 ctg cgc ggc ttc cag tgg gtt acg gga gac aac aac acc agc tat agc      510
Leu Arg Gly Phe Gln Trp Val Thr Gly Asp Asn Asn Thr Ser Tyr Ser
        90              95              100 agg tgg gca cgg ctc gac ctc aat ggg gct ccc ctc tgc ggc ccg ttg      558
Arg Trp Ala Arg Leu Asp Leu Asn Gly Ala Pro Leu Cys Gly Pro Leu
    105             110             115 tgc gtc gct gtc tcc gct gct gag gcc act gtg ccc agc gag ccg atc      606
Cys Val Ala Val Ser Ala Ala Glu Ala Thr Val Pro Ser Glu Pro Ile
120             125             130 tgg gag gag cag cag tgc gaa gtg aag gcc gat ggc ttc ctc tgc gag      654
Trp Glu Glu Gln Gln Cys Glu Val Lys Ala Asp Gly Phe Leu Cys Glu
135             140             145             150 ttc cac ttc cca gcc acc tgc agg cca ctg gct gtg gag ccc ggc gcc      702
Phe His Phe Pro Ala Thr Cys Arg Pro Leu Ala Val Glu Pro Gly Ala
            155             160             165 gcg gct gcc gcc gtc tcg atc acc tac ggc acc ccg ttc gcg gcc cgc      750
Ala Ala Ala Ala Val Ser Ile Thr Tyr Gly Thr Pro Phe Ala Ala Arg
        170             175             180 gga gcg gac ttc cag gcg ctg ccg gtg ggc agc tcc gcc gcg gtg gct      798
Gly Ala Asp Phe Gln Ala Leu Pro Val Gly Ser Ser Ala Ala Val Ala
    185             190             195 ccc ctc ggc tta cag cta atg tgc acc gcg ccg gga gcg gtc cag          846
Pro Leu Gly Leu Gln Leu Met Cys Thr Ala Pro Pro Gly Ala Val Gln
200             205             210 ggg cac tgg gcc agg gag gcg ccg ggc gct tgg gac tgc agc gtg gag      894
Gly His Trp Ala Arg Glu Ala Pro Gly Ala Trp Asp Cys Ser Val Glu
215             220             225             230 aac ggc ggc tgc gag cac gcg tgc aat gcg atc cct ggg gct ccc cgc      942
Asn Gly Gly Cys Glu His Ala Cys Asn Ala Ile Pro Gly Ala Pro Arg
            235             240             245 tgc cag tgc cca gcc ggc gcc gcc ctg cag gca gac ggg cgc tcc tgc      990
Cys Gln Cys Pro Ala Gly Ala Ala Leu Gln Ala Asp Gly Arg Ser Cys
        250             255             260 acc gca tcc gcg acg cag tcc tgc aac gac ctc tgc gag cac ttc tgc     1038
Thr Ala Ser Ala Thr Gln Ser Cys Asn Asp Leu Cys Glu His Phe Cys
    265             270             275 gtt ccc aac ccc gac cag ccg ggc tcc tac tcg tgc atg tgc gag acc     1086
Val Pro Asn Pro Asp Gln Pro Gly Ser Tyr Ser Cys Met Cys Glu Thr
280             285             290
```

-continued

| | | |
|---|---|---|
| ggc tac cgg ctg gcg gcc gac caa cac cgg tgc gag gac gtg gat gac<br>Gly Tyr Arg Leu Ala Ala Asp Gln His Arg Cys Glu Asp Val Asp Asp<br>295                                300                          305                            310 | 1134 |

```
ggc tac cgg ctg gcg gcc gac caa cac cgg tgc gag gac gtg gat gac      1134
Gly Tyr Arg Leu Ala Ala Asp Gln His Arg Cys Glu Asp Val Asp Asp
295                 300                 305                 310 tgc ata ctg gag ccc agt ccg tgt ccg cag cgc tgt gtc aac aca cag      1182
Cys Ile Leu Glu Pro Ser Pro Cys Pro Gln Arg Cys Val Asn Thr Gln
            315                 320                 325 ggt ggc ttc gag tgc cac tgc tac cct aac tac gac ctg gtg gac ggc      1230
Gly Gly Phe Glu Cys His Cys Tyr Pro Asn Tyr Asp Leu Val Asp Gly
        330                 335                 340 gag tgt gtg gag ccc gtg gac ccg tgc ttc aga gcc aac tgc gag tac      1278
Glu Cys Val Glu Pro Val Asp Pro Cys Phe Arg Ala Asn Cys Glu Tyr
    345                 350                 355 cag tgc cag ccc ctg aac caa act agc tac ctc tgc gtc tgc gcc gag      1326
Gln Cys Gln Pro Leu Asn Gln Thr Ser Tyr Leu Cys Val Cys Ala Glu
360                 365                 370 ggc ttc gcg ccc att ccc cac gag ccg cac agg tgc cag atg ttt tgc      1374
Gly Phe Ala Pro Ile Pro His Glu Pro His Arg Cys Gln Met Phe Cys
375                 380                 385                 390 aac cag act gcc tgt cca gcc gac tgc gac ccc aac acc cag gct agc      1422
Asn Gln Thr Ala Cys Pro Ala Asp Cys Asp Pro Asn Thr Gln Ala Ser
            395                 400                 405 tgt gag tgc cct gaa ggc tac atc ctg gac gac ggt ttc atc tgc acg      1470
Cys Glu Cys Pro Glu Gly Tyr Ile Leu Asp Asp Gly Phe Ile Cys Thr
        410                 415                 420 gac atc gac gag tgc gaa aac ggc ggc ttc tgc tcc ggg gtg tgc cac      1518
Asp Ile Asp Glu Cys Glu Asn Gly Gly Phe Cys Ser Gly Val Cys His
    425                 430                 435 aac ctc ccc ggt acc ttc gag tgc atc tgc ggg ccc gac tcg gcc ctt      1566
Asn Leu Pro Gly Thr Phe Glu Cys Ile Cys Gly Pro Asp Ser Ala Leu
440                 445                 450 gtc cgc cac att ggc acc gac tgt gac tcc ggc aag gtg gac ggt ggc      1614
Val Arg His Ile Gly Thr Asp Cys Asp Ser Gly Lys Val Asp Gly Gly
455                 460                 465                 470 gac agc ggc tct ggc gag ccc ccg ccc agc ccg acg ccc ggc tcc acc      1662
Asp Ser Gly Ser Gly Glu Pro Pro Pro Ser Pro Thr Pro Gly Ser Thr
            475                 480                 485 ttg act cct ccg gcc gtg ggg ctc gtg cat tcg ggc ttg ctc ata ggc      1710
Leu Thr Pro Pro Ala Val Gly Leu Val His Ser Gly Leu Leu Ile Gly
        490                 495                 500 atc tcc atc gcg agc ctg tgc ctg gtg gtg gcg ctt ttg gcg ctc ctc      1758
Ile Ser Ile Ala Ser Leu Cys Leu Val Val Ala Leu Leu Ala Leu Leu
    505                 510                 515 tgc cac ctg cgc aag aag cag ggc gcc gcc agg gcc aag atg gag tac      1806
Cys His Leu Arg Lys Lys Gln Gly Ala Ala Arg Ala Lys Met Glu Tyr
520                 525                 530 aag tgc gcg gcc cct tcc aag gag gta gtg ctg cag cac gtg cgg acc      1854
Lys Cys Ala Ala Pro Ser Lys Glu Val Val Leu Gln His Val Arg Thr
535                 540                 545                 550 gag cgg acg ccg cag aga ctc tgagcggcct ccgtccagga gcctggctcc         1905
Glu Arg Thr Pro Gln Arg Leu
            555 gtccaggagc ctgtgcctcc tcaccccag ctttgctacc aaagcacctt agctggcatt    1965 acagctggag aagaccctcc ccgcacccc caagctgttt tcttctattc catggctaac    2025 tgcgagggg gtgattagag ggaggagaat gagcctcggc ctcttccgtg acgtcactgg    2085 accactgggc aatgatggca attttgtaac gaagacacag actgcgattt gtcccaggtc   2145 ctcactaccg ggcgcaggag ggtgagcgtt attggtcggc agccttctgg gcagaccttg   2205 acctcgtggg ctagggatga ctaaaatatt tatttttttt aagtatttag gttttttgttt 2265
```

-continued

```
gtttcctttg ttcttacctg tatgtctcca gtatccactt tgcacagctc tccggtctct    2325
ctctctctac aaactcccac ttgtcatgtg acaggtaaac tatcttggtg aattttttt     2385 tcctagccct ctcacattta tgaagcaagc cccacttatt cccattctt cctagttttc     2445 tcctcccagg aactgggcca actcacctga gtcaccctac ctgtgcctga ccctacttct    2505
tttgctctta gctgtctgct cagacagaac ccctacatga aacagaaaca aaaacactaa    2565
aaataaaaat ggccatttgc tttttcacca gatttgctaa tttatcctga aatttcagat    2625
tcccagagca aaataatttt aaacaaaggt tgagatgtaa aagtattaa attgatgttg     2685 ctggactgtc atagaaatta cacccaaaga ggtatttatc tttactttta aacagtgagc    2745
ctgaattttg ttgctgtttt gatttgtact gaaaaatggt aattgttgct aatcttctta    2805
tgcaatttcc tttttgtta ttattactta tttttgacag tgttgaaaat gttcagaagg     2865
ttgctctaga ttgcgagaag agacaaacac ctcccaggag acagttcaag aaagcttcaa    2925
actgcatgat tcatgccaat tagcaattga ctgtcactgt tccttgtcac tggtagacca    2985
aaataaaacc gactctactg gtcttgtgga attgggagct tgggaatgga tcctggagga    3045
tgcccaatta gggcctagcc ttaatcaggt cctcagagaa tttctaccat ttcagagagg    3105
ccttttggaa tgtggcccct gaacaagaat tggaagctgc cctgcccatg ggagctggtt    3165
agaaatgcag aatcctaggc tccaccccat ccagttcatg agaatctata tttaacaaga    3225
tctgcagggg gtgtgtctgc tcagtaattt gaggacaacc attccagact gcttccaatt    3285
ttctggaata catgaaatat agatcagtta taagtagcag gccaagtcag gcccttattt    3345
tcaagaaact gaggaatttt ctttgtgtag ctttgctctt tggtagaaaa ggctaggtac    3405
acagctctag acactgccac acagggtctg caaggtcttt ggttcagcta agccggaatt    3465
c                                                                   3466
```

<210> SEQ ID NO 2
<211> LENGTH: 575
<212> TYPE: PRT
<213> ORGANISM: Homo sapiens

<400> SEQUENCE: 2

```
Met Leu Gly Val Leu Val Leu Gly Ala Leu Ala Leu Ala Gly Leu Gly
         -15                 -10                  -5

Phe Pro Ala Pro Ala Glu Pro Gln Pro Gly Gly Ser Gln Cys Val Glu
 -1   1               5                  10

His Asp Cys Phe Ala Leu Tyr Pro Gly Pro Ala Thr Phe Leu Asn Ala
 15              20                  25                      30

Ser Gln Ile Cys Asp Gly Leu Arg Gly His Leu Met Thr Val Arg Ser
                 35                  40                  45

Ser Val Ala Ala Asp Val Ile Ser Leu Leu Leu Asn Gly Asp Gly Gly
             50                  55                  60

Val Gly Arg Arg Arg Leu Trp Ile Gly Leu Gln Leu Pro Pro Gly Cys
         65                  70                  75

Gly Asp Pro Lys Arg Leu Gly Pro Leu Arg Gly Phe Gln Trp Val Thr
     80                  85                  90

Gly Asp Asn Asn Thr Ser Tyr Ser Arg Trp Ala Arg Leu Asp Leu Asn
 95                 100                 105                 110

Gly Ala Pro Leu Cys Gly Pro Leu Cys Val Ala Val Ser Ala Ala Glu
                115                 120                 125

Ala Thr Val Pro Ser Glu Pro Ile Trp Glu Glu Gln Gln Cys Glu Val
            130                 135                 140
```

-continued

```
Lys Ala Asp Gly Phe Leu Cys Glu Phe His Phe Pro Ala Thr Cys Arg
        145                 150                 155
Pro Leu Ala Val Glu Pro Gly Ala Ala Ala Ala Val Ser Ile Thr
    160                 165                 170
Tyr Gly Thr Pro Phe Ala Ala Arg Gly Ala Asp Phe Gln Ala Leu Pro
175                 180                 185                 190
Val Gly Ser Ser Ala Ala Val Ala Pro Leu Gly Leu Gln Leu Met Cys
            195                 200                 205
Thr Ala Pro Pro Gly Ala Val Gln Gly His Trp Ala Arg Glu Ala Pro
            210                 215                 220
Gly Ala Trp Asp Cys Ser Val Glu Asn Gly Gly Cys Glu His Ala Cys
            225                 230                 235
Asn Ala Ile Pro Gly Ala Pro Arg Cys Gln Cys Pro Ala Gly Ala Ala
    240                 245                 250
Leu Gln Ala Asp Gly Arg Ser Cys Thr Ala Ser Ala Thr Gln Ser Cys
255                 260                 265                 270
Asn Asp Leu Cys Glu His Phe Cys Val Pro Asn Pro Asp Gln Pro Gly
            275                 280                 285
Ser Tyr Ser Cys Met Cys Glu Thr Gly Tyr Arg Leu Ala Ala Asp Gln
            290                 295                 300
His Arg Cys Glu Asp Val Asp Asp Cys Ile Leu Glu Pro Ser Pro Cys
            305                 310                 315
Pro Gln Arg Cys Val Asn Thr Gln Gly Gly Phe Glu Cys His Cys Tyr
    320                 325                 330
Pro Asn Tyr Asp Leu Val Asp Gly Glu Cys Val Glu Pro Val Asp Pro
335                 340                 345                 350
Cys Phe Arg Ala Asn Cys Glu Tyr Gln Cys Gln Pro Leu Asn Gln Thr
            355                 360                 365
Ser Tyr Leu Cys Val Cys Ala Glu Gly Phe Ala Pro Ile Pro His Glu
            370                 375                 380
Pro His Arg Cys Gln Met Phe Cys Asn Gln Thr Ala Cys Pro Ala Asp
            385                 390                 395
Cys Asp Pro Asn Thr Gln Ala Ser Cys Glu Cys Pro Glu Gly Tyr Ile
    400                 405                 410
Leu Asp Asp Gly Phe Ile Cys Thr Asp Ile Asp Glu Cys Glu Asn Gly
415                 420                 425                 430
Gly Phe Cys Ser Gly Val Cys His Asn Leu Pro Gly Thr Phe Glu Cys
            435                 440                 445
Ile Cys Gly Pro Asp Ser Ala Leu Val Arg His Ile Gly Thr Asp Cys
            450                 455                 460
Asp Ser Gly Lys Val Asp Gly Gly Asp Ser Gly Ser Gly Glu Pro Pro
            465                 470                 475
Pro Ser Pro Thr Pro Gly Ser Thr Leu Thr Pro Ala Val Gly Leu
    480                 485                 490
Val His Ser Gly Leu Leu Ile Gly Ile Ser Ile Ala Ser Leu Cys Leu
495                 500                 505                 510
Val Val Ala Leu Leu Ala Leu Leu Cys His Leu Arg Lys Lys Gln Gly
            515                 520                 525
Ala Ala Arg Ala Lys Met Glu Tyr Lys Cys Ala Ala Pro Ser Lys Glu
            530                 535                 540
Val Val Leu Gln His Val Arg Thr Glu Arg Thr Pro Gln Arg Leu
            545                 550                 555
```

-continued

```
<210> SEQ ID NO 3
<211> LENGTH: 33
<212> TYPE: DNA
<213> ORGANISM: artificial sequence
<220> FEATURE:
<223> OTHER INFORMATION: primer1034

<400> SEQUENCE: 3
ccgggatcct caacagtcgg tgccaatgtg gcg                          33

<210> SEQ ID NO 4
<211> LENGTH: 33
<212> TYPE: DNA
<213> ORGANISM: artificial sequence
<220> FEATURE:
<223> OTHER INFORMATION: primer1033

<400> SEQUENCE: 4
ccgggatcct gcagcgtgga gaacggcggc tgc                          33

<210> SEQ ID NO 5
<211> LENGTH: 55
<212> TYPE: DNA
<213> ORGANISM: artificial sequence
<220> FEATURE:
<223> OTHER INFORMATION: template

<400> SEQUENCE: 5
ccccacgagc gcacaggtg ccagctgttt tgcaaccaga ctgcctgtcc agccg    55

<210> SEQ ID NO 6
<211> LENGTH: 28
<212> TYPE: DNA
<213> ORGANISM: artificial sequence
<220> FEATURE:
<223> OTHER INFORMATION: template

<400> SEQUENCE: 6
cgagtgccac tgtgcaccta actacgac                                28

<210> SEQ ID NO 7
<211> LENGTH: 30
<212> TYPE: DNA
<213> ORGANISM: artificial sequence
<220> FEATURE:
<223> OTHER INFORMATION: template

<400> SEQUENCE: 7
cactgctacc ctgcatatga cctggtggac                              30

<210> SEQ ID NO 8
<211> LENGTH: 30
<212> TYPE: DNA
<213> ORGANISM: artificial sequence
<220> FEATURE:
<223> OTHER INFORMATION: template

<400> SEQUENCE: 8
ccactgctac ccgaatgccg acctggtgga                              30

<210> SEQ ID NO 9
<211> LENGTH: 29
<212> TYPE: DNA
<213> ORGANISM: artificial sequence
<220> FEATURE:
<223> OTHER INFORMATION: template
```

```
<400> SEQUENCE: 9
ctaccctaac tatgcattgg tggacggcg                                    29

<210> SEQ ID NO 10
<211> LENGTH: 30
<212> TYPE: DNA
<213> ORGANISM: artificial sequence
<220> FEATURE:
<223> OTHER INFORMATION: template

<400> SEQUENCE: 10
cctaactacg acgcggtcga cggcgagtgt                                   30

<210> SEQ ID NO 11
<211> LENGTH: 38
<212> TYPE: DNA
<213> ORGANISM: artificial sequence
<220> FEATURE:
<223> OTHER INFORMATION: template

<400> SEQUENCE: 11
actacgacct ggcggacggc gaatgcgtgg agcccgtg                          38

<210> SEQ ID NO 12
<211> LENGTH: 35
<212> TYPE: DNA
<213> ORGANISM: artificial sequence
<220> FEATURE:
<223> OTHER INFORMATION: template

<400> SEQUENCE: 12
acgacctggt ggccggcgaa tgcgtggagc ccgtg                             35

<210> SEQ ID NO 13
<211> LENGTH: 29
<212> TYPE: DNA
<213> ORGANISM: artificial sequence
<220> FEATURE:
<223> OTHER INFORMATION: template

<400> SEQUENCE: 13
tggtggacgg cgcatgcgtg gagcccgtg                                    29

<210> SEQ ID NO 14
<211> LENGTH: 46
<212> TYPE: DNA
<213> ORGANISM: artificial sequence
<220> FEATURE:
<223> OTHER INFORMATION: template

<400> SEQUENCE: 14
ggcgagtgtg tggagcccgt ggcgccgtgc ttcagagcca actgcg                 46

<210> SEQ ID NO 15
<211> LENGTH: 47
<212> TYPE: DNA
<213> ORGANISM: artificial sequence
<220> FEATURE:
<223> OTHER INFORMATION: template

<400> SEQUENCE: 15
cccgtgcttc agagccaact gcgcatacca gtgccagccc ctgaacc                47

<210> SEQ ID NO 16
<211> LENGTH: 36
```

-continued

```
<212> TYPE: DNA
<213> ORGANISM: artificial sequence
<220> FEATURE:
<223> OTHER INFORMATION: template

<400> SEQUENCE: 16
gccaactgcg aggcccagtg tcaacccctg aaccaa                                    36

<210> SEQ ID NO 17
<211> LENGTH: 26
<212> TYPE: DNA
<213> ORGANISM: artificial sequence
<220> FEATURE:
<223> OTHER INFORMATION: primer

<400> SEQUENCE: 17
gcgcccattc ccggcgagcc gcacag                                               26

<210> SEQ ID NO 18
<211> LENGTH: 26
<212> TYPE: DNA
<213> ORGANISM: artificial sequence
<220> FEATURE:
<223> OTHER INFORMATION: primer

<400> SEQUENCE: 18
ctgtgcggct cgccgggaat gggcgc                                               26
```